(12) United States Patent
Hwang et al.

(10) Patent No.: US 10,646,498 B2
(45) Date of Patent: May 12, 2020

(54) COMPOSITION FOR PREVENTING, ALLEVIATING OR TREATING MUSCLE DISEASES OR IMPROVING MUSCULAR FUNCTION

(71) Applicant: AAT COSTECH CO., LTD., Seoul (KR)

(72) Inventors: Jae Kwan Hwang, Seoul (KR); Chang Hee Kim, Seoul (KR); Mi-Bo Kim, Seoul (KR)

(73) Assignee: AAT COSTECH CO., LTD., Seoul (KR)

( * ) Notice: Subject to any disclaimer, the term of this patent is extended or adjusted under 35 U.S.C. 154(b) by 0 days.

(21) Appl. No.: 15/577,098

(22) PCT Filed: May 26, 2016

(86) PCT No.: PCT/KR2016/005597
§ 371 (c)(1),
(2) Date: May 2, 2018

(87) PCT Pub. No.: WO2016/190689
PCT Pub. Date: Dec. 1, 2016

(65) Prior Publication Data
US 2018/0318320 A1 Nov. 8, 2018

(30) Foreign Application Priority Data

May 26, 2015 (KR) .......................... 10-2015-0072740
May 26, 2016 (KR) .......................... 10-2016-0064917

(51) Int. Cl.
| | | |
|---|---|---|
| A61K 31/575 | (2006.01) | |
| A61P 21/00 | (2006.01) | |
| A61K 36/03 | (2006.01) | |

(52) U.S. Cl.
CPC ............ *A61K 31/575* (2013.01); *A61K 36/03* (2013.01); *A61P 21/00* (2018.01)

(58) Field of Classification Search
CPC ...... A61K 31/575; A61K 36/03; A61K 31/56; A61K 2300/00; A61P 21/00
See application file for complete search history.

(56) References Cited

FOREIGN PATENT DOCUMENTS

| EP | 2699391 A1 * | 2/2014 | ............ A61K 31/56 |
|---|---|---|---|
| JP | 2009-191008 | 8/2009 | |
| KR | 10-2000-0063617 | 11/2000 | |
| KR | 10-2005-0006533 | 1/2005 | |
| KR | 10-2014-0060106 | 5/2014 | |
| KR | 10-2014-0081339 | 7/2014 | |
| KR | 10-2014-0131100 | 11/2014 | |
| WO | WO-2014098512 A1 * | 6/2014 | ............ A61K 31/56 |

OTHER PUBLICATIONS

Kwan et al., J Aging Res. 2013; Epub Mar. 13, 2013 (Year: 2013).*
Jung et al., Food and Chemical Toxicology, vol. 59, Sep. 2013, pp. 199-206. (Year: 2013).*
Askanas et al., Biochemica et Biophysica Acta (BBA)—Molecular Basis of Disease, vol. 1852, Issue 4, Apr. 2015, pp. 633-643, available online Sep. 18, 2014. (Year: 2014).*
Demontis et al., "Mechanisms of skeletal muscle aging: insights from *Drosophila* and mammalian models," *Disease Models & Mechanisms*, 2013; 6:1339-1352.
Hornberger, Troy. "Mechanotransduction and the Regulation of mTORC1 Signaling in Skeletal Muscles," *Intl. J. Biochem. Cell Biol.* 2011; 43(9): 1267-1276.
International Search Report and Written Opinion issued in Application No. PCT/KR2016/005597, dated Nov. 28, 2015.
Lee et al., "The role of hormones, cytokines and heat shock proteins during age-related muscle loss," *Clinical Nutrition*, 2007; 26(5): 524-534. (Abstract Only).
McKinnell et al., "Molecular Mechanism of Muscle Atrophy," *Cell*, 2004; 119: 907-910.
Nader, Gustavo. "Molecular determinants of skeletal muscle mass: getting 'AKT' together," *The International Journal of Biochemistry & Cell Biology*, 2005; 37(10): 1985-1996 (Abstract Only).
Zanou et al., "Skeletal muscle hypertrophy and regeneration: interplay between the myogenic regulatory factors (MRFs) and insulin-like growth factors (IGFs) pathways," *Cell. Mol. Life Sci.* 2013; 70: 4117-4130 (Abstract Only).
Cai et al., "Minocycline alleviates beta-amyloid protein and tau pathology via restraining neuroinflammation induced by diabetic metabolic disorder" *Clinical Interventions in Aging*, 2013, 8:1089-1095.

(Continued)

*Primary Examiner* — Jean P Cornet
(74) *Attorney, Agent, or Firm* — Norton Rose Fulbright US LLP

(57) ABSTRACT

A composition for preventing or treating muscle diseases or improving muscular function, containing fucosterol, *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract is disclosed. Fucosterol, *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract increases the protein expression of p-mTOR, which is a main gene involved in muscle protein synthesis, inhibits the mRNA expression of MuRF-1 and atrogin-1 involved in muscle protein degradation, and increases the mRNA expression of MyoD and myogenin involved in muscle differentiation, thereby having an effect of remarkably increasing muscular function. In addition, the composition can be safely used without side effects, thereby being usable in medicine, food, cosmetic products, livestock feed, a feed additive and the like.

13 Claims, 4 Drawing Sheets
Specification includes a Sequence Listing.

(56) References Cited

OTHER PUBLICATIONS

Choi et al., "Synergistic Action of Flavonoids, Baicalein, and Daidzein in Estrogenic and Neuroprotective Effects: A Development of Potential Health Products and Therapeutic Drugs against Alzheimer's Disease" *Evidence-Based Complementary and Alternative Medicine*, 2013, Article IDS 635694, 10 pages.

Cox et al., "Dietary (−)-epicatechin as a potent inhibitor of βγ-secretase amyloid precursor protein processing" *Neurobiology of Aging*, 2015, 36:178-187.

Ikemoto et al., "A Relative High Dose of Vitamin E Does Not Attenuate Unweighting-Induced Oxidative Stress and Ubiquitination in Rate Skeletal Muscle" *Journal of Physiological Anthropology*, 2002, 21(5):257-263.

Komrakova et al., "Effect of daidzein, 4-methylbenzylidene camphor or estrogen on gastrocnemius muscle of osteoporotic rats undergoing tibia healing period," *Journal of Endocrinology*, 2009, 201:253-262.

Nogueira et al., "(−)-Epicatechin enhances fatigue resistance and oxidative capacity in mouse muscle" *J. Physiol*, 2011, 589(18):4615-4631.

Norden et al., "Tumor growth increases neuroinflammation, fatigue and depressive-like behavior prior to alterations in muscle function," *Brain, Behavior, and Immunity*, 2015, 43:76-85.

Sung et al., "Early vitamin E supplementation in young but not aged mice reduces Aβ levels and amyloid deposition in a transgenic model of Alzheimer's disease" *The FASEB Journal*, 2017, 18(2):323-325.

\* cited by examiner

COMPOSITION FOR PREVENTING, ALLEVIATING OR TREATING MUSCLE DISEASES OR IMPROVING MUSCULAR FUNCTION

CROSS-REFERENCE TO RELATED APPLICATIONS

This application is a national phase application under 35 U.S.C. § 371 of International Application No. PCT/KR2016/005597, filed May 26, 2016, which claims priority to and the benefit of Korean Patent Application Nos. 10-2015-0072740 and 10-2016-0064917 filed on May 26, 2015 and May 26, 2016, respectively, the disclosures of which are incorporated herein by reference in their entirety.

FIELD OF THE DISCLOSURE

The present invention relates to a composition for preventing, alleviating or treating muscle diseases or improving muscular function, and more particularly, to a composition for preventing, alleviating or treating muscle diseases or improving muscular function, which includes fucosterol, *Sargassum fulvellum*, a *Sargassum fulvellum* dried powder, a *Sargassum fulvellum* extract, *Sargassum fusiforme*, a *Sargassum fusiforme* dried powder, or a *Sargassum fusiforme* extract.

DESCRIPTION OF RELATED ART

Muscle atrophy is caused by a gradual decrease in the mass of muscle, and refers to the weakness and degeneration of muscles (Cell, 119(7): 907-910, 2004). Muscle atrophy is induced by inactivity, oxidative stress, chronic inflammation, and the like and serves to weaken muscle functions and motor abilities (Clinical Nutrition, 26(5): 524-534, 2007). The most important factor in determining muscle functionality is muscle mass, which is maintained by the balance between the synthesis and degradation of proteins. Muscular atrophy develops when protein degradation exceeds protein synthesis (The International Journal of Biochemistry and Cell Biology, 37(10): 1985-1996, 2005).

The size of muscles is regulated by intracellular signaling pathways which induce anabolism or catabolism occurring in the muscles, and an increase in synthesis of muscle proteins is caused when a signaling response inducing the synthesis of the muscle proteins rather than the degradation of the muscle proteins occurs, which results in an increased size of muscles (hypertrophy) or an increased number of muscular fibers (hyperplasia) according to the increase in muscle proteins (The Korea Journal of Sports Science, 20(3): 1551-1561, 2011).

Factors involved in muscle protein synthesis induce the synthesis of proteins by phosphorylating downstream proteins using the stimulation of a phosphatidylinositol-3 kinase (PI3K)/Akt pathway as a starting point in myocytes. The activity of a mammalian target of rapamycin (mTOR) through PI3K/Akt signaling has been recognized as a key growth signaling factor that integrates various growth signals in cells. mTOR contributes to an increase in muscle mass by activating two factors that initiate mRNA translation, that is, 4E-binding protein (4E-BP1) and phosphorylated 70-kDa ribosomal S6 kinase (p70S6K), to induce muscle protein synthesis (The Korea Journal of Sports Science, 20(3): 1551-1561, 2011; The International Journal of Biochemistry and Cell Biology, 43(9): 1267-1276, 2011). On the contrary, forkhead box (FoxO) which is a transcription factor increases the expression of E3 ubiquitin ligase factors atrogin-1 and MuRF-1, which are associated with the degradation of proteins, when FoxO migrates from the protoplasm into the nucleus (Disease Models and Mechanisms, 6: 25-39, 2013). Their increased expression levels promote the degradation of proteins in muscles, resulting in a reduced mass of the muscles. Therefore, promoting mTOR activity and inhibiting atrogin-1 and MuRF-1 expression cause an increase in the amount of muscle proteins, which leads to an increased mass of the muscles. Muscle cell differentiation and muscle formation are regulated by various muscle regulatory factors. Among these, MyoD serves to initiate the expression of muscle-specific genes and induce the differentiation of muscle satellite cells into myoblasts. The induction of myogenin expression through the activity of MyoD is the most important factor for the fusion of myoblasts, and is involved in the formation of myotubes. Muscular fibers formed through such a process are finally bundled to form muscles (Cellular and Molecular Life Sciences, 70: 4117-4130, 2013).

*Sargassum fulvellum* is a marine alga that belongs to the genus *Sargassum*. To date, *Sargassum fulvellum* has been reported to have activities such as anti-bacterial activity (Korean Journal of Food Science and Technology, 42(2): 155-159, 2010), anti-inflammatory activity (Journal of Ethnopharmacology, 116(1): 187-190, 2008), anti-oxidative activity (Journal of Food Science and Nutrition, 12(2): 65-73, 2007), anti-cancer activity (Chemotherapy, 32(12): 1004-1009, 1984), anti-photoaging activity (Evidence-based Complementary and Alternative Medicine, 2013: 747846, 2013), anti-diabetic activity (Natural Product Sciences, 18(2): 130-136, 2012), and the like.

*Sargassum fusiforme* is a marine alga that belongs to the genus *Sargassum*. To date, *Sargassum fusiforme* has been reported to have activities such as anti-oxidative and anti-inflammatory activities (Tropical Journal of Pharmaceutical Research, 14(3): 463-468, 2015), anti-diabetic activity (Food Science and Biotechnology, 23(3): 2037-2044, 2014), anti-viral activity (Natural Medicines, 48(3): 173-179, 1994), anti-cancer activity (Journal of Medicinal Food, 12(4): 782-787, 2009), anti-osteoporotic activity (Journal of Medicinal Food, 15(4): 384-390, 2012), and the like.

Fucosterol is a material that is abundantly present in marine algae including *Sargassum fulvellum* and *Sargassum fusiforme*, and is often found in marine algae which grow in coastal areas of Asia such as Korea, China, Japan, and the like. To date, fucosterol has been reported to have activities such as anti-cancer activity (Pharmacognosy Magazine, 8(29): 60-64, 2012), anti-diabetic activity (Archives of Pharmacal Research, 27(11): 1120-1122, 2004), anti-oxidative activity (Bioorganic and Medicinal Chemistry, 17(5): 1963-1973, 2009), an activity of improving blood lipid profiles (Biochemical and Biophysical Research Communications, 369(2): 363-368, 2008), an activity of improving cholesterol metabolism (New Phytologist, 183(2): 291-300, 2009), anti-bacterial activity (Journal of Pharmaceutical and Biomedical Analysis, 51(2): 450-4555, 2010), antifungal activity (Natural Product Research, 24(15): 1481-1487, 2010), antiaging activity (Photochemistry and Photobiology, 89(4): 911-918, 2013), and the like.

Prior to the present invention, however, there is no report on the use of fucosterol, *Sargassum fulvellum* or *Sargassum fusiforme* for preventing, alleviating or treating muscle diseases or improving muscular function.

SUMMARY OF THE INVENTION

Therefore, the present inventors have searched for natural substances that have an excellent activity of regulating muscular function and can be safely applied, and found that fucosterol, *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract has an activity of preventing, alleviating or treating muscle diseases or improving muscular function. Therefore, the present invention has been completed based on the facts.

Therefore, it is an aspect of the present invention to provide a pharmaceutical composition for preventing or treating muscle diseases, which includes a fucosterol compound represented by the following Formula 1 or a *Sargassum fulvellum* or *Sargassum fusiforme* extract including the same as an active ingredient:

[Formula 1]

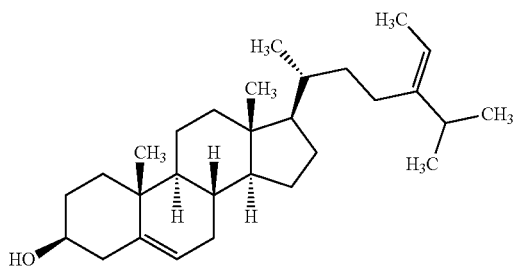

It is another aspect of the present invention to provide a pharmaceutical composition for preventing or treating muscle diseases, which includes *Sargassum fulvellum* or a dried powder or extract thereof as an active ingredient.

It is still another aspect of the present invention to provide a pharmaceutical composition for preventing or treating muscle diseases, which includes *Sargassum fusiforme* or a dried powder or extract thereof as an active ingredient.

It is yet another aspect of the present invention to provide a health functional food composition for preventing or alleviating muscle diseases, which includes a fucosterol compound represented by the following Formula 1 or a *Sargassum fulvellum* or *Sargassum fusiforme* extract including the same as an active ingredient:

[Formula 1]

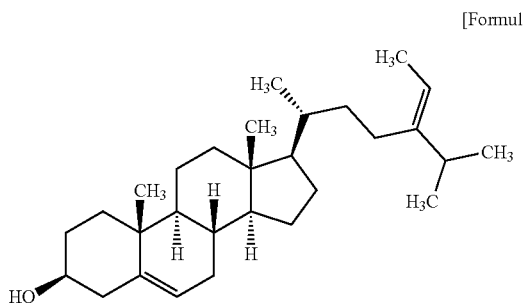

It is yet another aspect of the present invention to provide a health functional food composition for preventing or alleviating muscle diseases, which includes *Sargassum fulvellum* or a dried powder or extract thereof as an active ingredient.

It is yet another aspect of the present invention to provide a health functional food composition for preventing or alleviating muscle diseases, which includes *Sargassum fusiforme* or a dried powder or extract thereof as an active ingredient.

It is yet another aspect of the present invention to provide a cosmetic composition for improving muscular function, which includes a fucosterol compound represented by the following Formula 1 or a *Sargassum fulvellum* or *Sargassum fusiforme* extract including the same as an active ingredient:

[Formula 1]

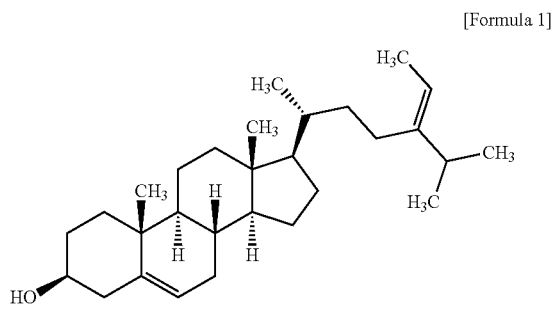

It is yet another aspect of the present invention to provide a cosmetic composition for improving muscular function, which includes *Sargassum fulvellum* or a dried powder or extract thereof as an active ingredient.

It is yet another aspect of the present invention to provide a cosmetic composition for improving muscular function, which includes *Sargassum fusiforme* or a dried powder or extract thereof as an active ingredient.

It is yet another aspect of the present invention to provide a feed additive for preventing or alleviating muscle diseases, which includes a fucosterol compound represented by the following Formula 1 or a *Sargassum fulvellum* or *Sargassum fusiforme* extract including the same as an active ingredient:

[Formula 1]

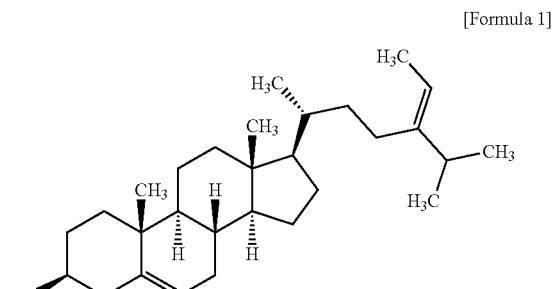

It is yet another aspect of the present invention to provide a feed additive for preventing or alleviating muscle diseases, which includes *Sargassum fulvellum* or a dried powder or extract thereof as an active ingredient.

It is yet another aspect of the present invention to provide a feed additive for preventing or alleviating muscle diseases, which includes *Sargassum fusiforme* or a dried powder or extract thereof as an active ingredient.

To solve the above problems, according to an aspect of the present invention, there is provided a pharmaceutical composition for preventing or treating muscle diseases, which includes a fucosterol compound represented by the following Formula 1 or a *Sargassum fulvellum* or *Sargassum fusiforme* extract including the same as an active ingredient:

[Formula 1]

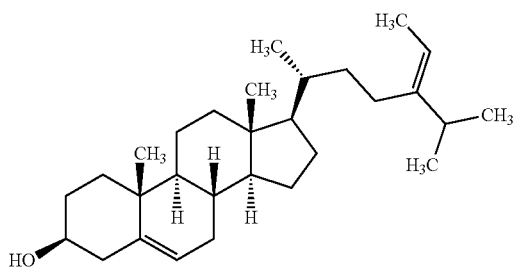

According to another aspect of the present invention, there is provided a pharmaceutical composition for preventing or treating muscle diseases, which includes *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract as an active ingredient.

According to still another aspect of the present invention, there is provided a health functional food composition for preventing or alleviating muscle diseases, which includes a fucosterol compound represented by the following Formula 1 or a *Sargassum fulvellum* or *Sargassum fusiforme* extract including the same as an active ingredient:

[Formula 1]

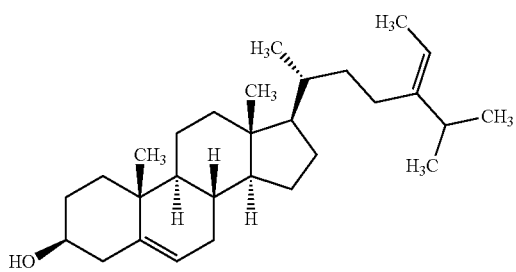

According to yet another aspect of the present invention, there is provided a health functional food composition for preventing or alleviating muscle diseases, which includes *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract as an active ingredient.

According to yet another aspect of the present invention, there is provided a cosmetic composition for improving muscular function, which includes a fucosterol compound represented by the following Formula 1 or a *Sargassum fulvellum* or *Sargassum fusiforme* extract including the same as an active ingredient:

[Formula 1]

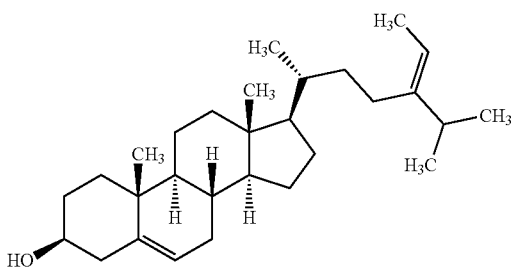

According to yet another aspect of the present invention, there is provided a cosmetic composition for improving muscular function, which includes *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract as an active ingredient.

According to yet another aspect of the present invention, there is provided a feed additive for preventing or alleviating muscle diseases, which includes a fucosterol compound represented by the following Formula 1 or a *Sargassum fulvellum* or *Sargassum fusiforme* extract including the same as an active ingredient:

[Formula 1]

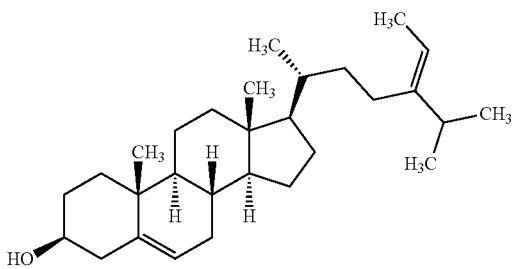

According to yet another aspect of the present invention, there is provided a feed additive for preventing or alleviating muscle diseases, which includes a *Sargassum fulvellum* or *Sargassum fusiforme* extract as an active ingredient.

According to one preferred embodiment of the present invention, the fucosterol represented by Formula 1 may be isolated from the *Sargassum fulvellum* or *Sargassum fusiforme* extract.

According to one preferred embodiment of the present invention, the extract may be obtained by extracting *Sargassum fulvellum* or *Sargassum fusiforme* with one or more solvents selected from the group consisting of water, an organic solvent having 1 to 6 carbon atoms, a subcritical fluid, and a supercritical fluid.

According to another preferred embodiment of the present invention, the organic solvent having 1 to 6 carbon atoms may include one or more selected from the group consisting of an alcohol having 1 to 6 carbon atoms, acetone, ether, benzene, chloroform, ethyl acetate, methylene chloride, hexane, cyclohexane, and petroleum ether.

According to still another preferred embodiment of the present invention, the extract may be obtained by extracting *Sargassum fulvellum* or *Sargassum fusiforme* under a condition of an ultra-high pressure of 100 MPa to 1,000 MPa.

According to yet another preferred embodiment of the present invention, the muscle diseases may include one or more selected from the group consisting of atony, muscular atrophy, muscular dystrophy, muscular degeneration, myasthenia, cachexia, and sarcopenia.

According to the present invention, fucosterol, *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract can increase the protein expression of p-mTOR involved in muscle protein synthesis, inhibit the mRNA expression of MuRF-1 and atrogin-1 involved in muscle protein degradation, and increase the mRNA expression of MyoD and myogenin involved in muscle differentiation, and thus can be highly effective in remarkably increasing muscle mass. Also, because the composition of the present invention is a natural product, the composition can be safely used without side effects, and thus can be used in medicines, foods, cosmetic products, livestock feeds, feed additives and the like.

DETAILED DESCRIPTION OF THE INVENTION

Figure 1:
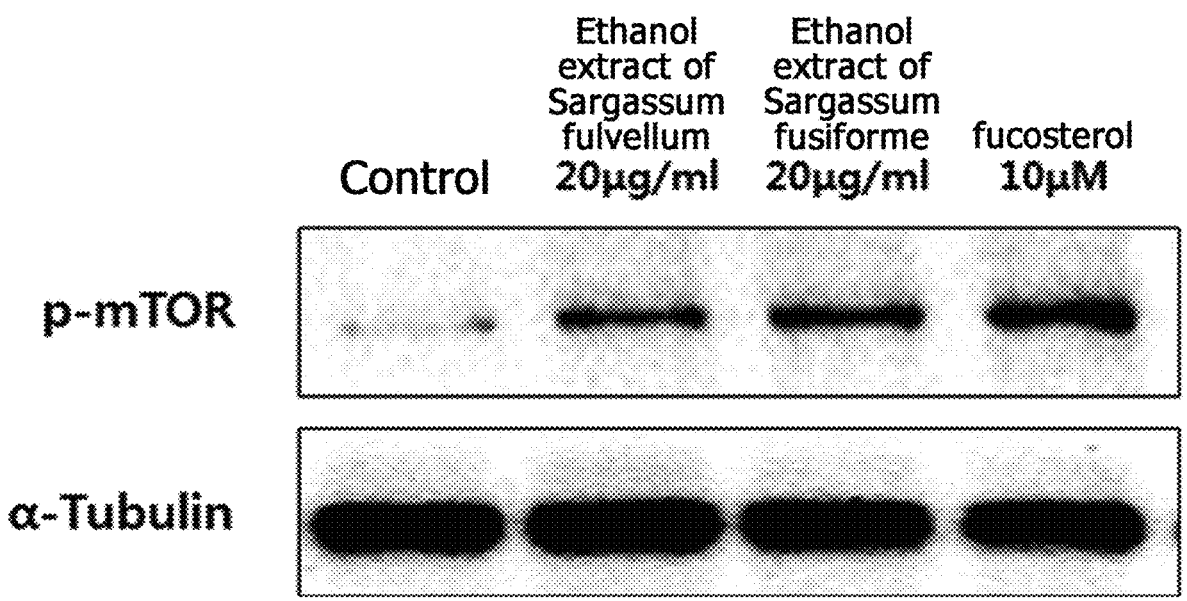
FIG. 1 shows results of measuring the protein expression of p-mTOR in L6 muscle cells when the L6 muscle cells are treated with an ethanol extract of *Sargassum fulvellum*, an ethanol extract of *Sargassum fusiforme* or fucosterol.

Hereinafter, the present invention will be described in detail.

The present invention provides a use of fucosterol represented by the following Formula 1, a *Sargassum fulvellum* extract or a *Sargassum fusiforme* extract for preventing, alleviating or treating muscle diseases or improving muscular function; a composition for preventing, alleviating or treating muscle diseases or improving muscular function, which includes fucosterol represented by the following Formula 1, *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract; or a method of preventing, alleviating or treating muscle diseases or improving muscular function, which includes applying fucosterol represented by the following Formula 1, a *Sargassum fulvellum* extract or a *Sargassum fusiforme* extract to a mammal including a human:

[Formula 1]

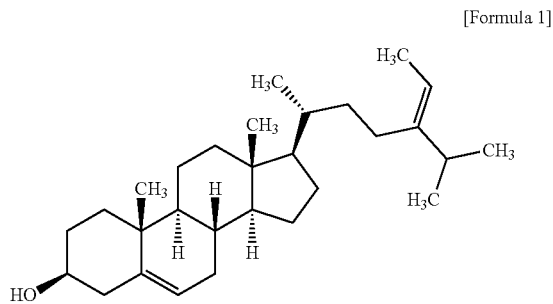

In this specification, the term '*Sargassum fulvellum*' refers to a marine alga that belongs to the *Sargassum* spp. of the family Helotiaceae.

In this specification, the term '*Sargassum fusiforme*' refers to a marine alga that belongs to the *Sargassum* spp. of the family Helotiaceae.

In this specification, the '*Sargassum fulvellum* dried powder' or '*Sargassum fusiforme* dried powder' may be prepared by grinding dried *Sargassum fulvellum* or *Sargassum fusiforme* using a method that may be readily carried out by a person having ordinary skill in the art to which the present invention belongs, so that a mammal including a human can easily eat the dried powder and an active ingredient can be easily released from the dried powder in the intestines after ingestion, thereby promoting an easy absorption of the active ingredient into the body of the mammal. For this purpose, the particle shape or size of the dried powder is not limited. However, it is desirable that the dried powder is possibly prepared in a fine powder form because the aforementioned active ingredient is more easily released as a particle surface of the dried dried powder is maximized. According to one exemplary embodiment of the present invention, the dried powder is prepared by grinding the dried *Sargassum fulvellum* or *Sargassum fusiforme* using a mixer.

In this specification, the '*Sargassum fulvellum* extract' is obtained by extracting *Sargassum fulvellum* with a suitable solvent, and includes all types of dried products, which are obtained by drying an extraction solution or a diluted or concentrated solution of the extraction solution, or crude purified products or purified products thereof. A method of preparing a *Sargassum fulvellum* extract may include extracting *Sargassum fulvellum* with one or more solvents selected from the group consisting of water, an organic solvent having 1 to 6 carbon atoms, and a subcritical or supercritical fluid, but the present invention is not limited thereto.

In this specification, the '*Sargassum fusiforme* extract' is obtained by extracting *Sargassum fusiforme* using a suitable solvent, and includes all types of dried products, which are obtained by drying an extraction solution or a diluted or concentrated solution of the extraction solution, or crude purified products or purified products thereof. A method of preparing a Sargassum fusiforme extract may include extracting Sargassum fusiforme with one or more solvents selected from the group consisting of water, an organic solvent having 1 to 6 carbon atoms, and a subcritical or supercritical fluid, but the present invention is not limited thereto.

The Sargassum fulvellum or Sargassum fusiforme extract of the present invention may be prepared using conventional extraction methods known in the related art, such as thermal extraction, cold extraction, ultrasonic extraction, filtration, and reflux extraction methods, and commercially available Sargassum fulvellum and Sargassum fusiforme may be purchased and used as the Sargassum fulvellum and Sargassum fusiforme, or naturally collected or cultivated Sargassum fulvellum and Sargassum fusiforme may be used as the Sargassum fulvellum and Sargassum fusiforme.

The Sargassum fulvellum or Sargassum fusiforme extract according to the present invention may be isolated using a conventional method of preparing an extract from a natural product as known in the related art, that is, isolated using a conventional solvent under conventional temperature and pressure conditions.

The term "fraction" used in this specification refers to a product obtained by a fractionation method of isolating a certain component or a certain group from a mixture including various components. In the present invention, the fraction refers to a product obtained by a fractionation method of isolating a certain component or a certain group from the Sargassum fulvellum or Sargassum fusiforme extract thus prepared.

To obtain the Sargassum fulvellum or Sargassum fusiforme extract according to the present invention, conventional fractionation solvents known in the related art, for example, polar solvents such as water, an anhydrous or hydrated lower alcohol having 1 to 4 carbon atoms (e.g., ethanol, methanol, and the like), and the like, and non-polar solvents such as hexane, butanol, ethyl acetate, chloroform, dichloromethane, and the like, or mixed solvents thereof may be used, but the present invention is not limited thereto.

A Sargassum fulvellum or Sargassum fusiforme fraction of the present invention may also include what is obtained by additionally applying a purification process. For example, the Sargassum fulvellum or Sargassum fusiforme fraction of the present invention also includes fractions obtained by filtering the Sargassum fulvellum or Sargassum fusiforme extract according to the present invention through a filtration membrane having a predetermined molecular weight cut-off value, fractions obtained by various purification methods further carried out, such as separation by various types of chromatography (manufactured for separation based on size, charge, hydrophobicity or affinity), and the like.

In this specification, the term 'muscle' generally refers to all types of ligaments, muscles, and tendons, and the term 'muscular function' refers to an ability of a muscle to exert a force by contraction, and includes muscular strength which is an ability of a muscle to exert a contractile force to the maximum in order to overcome resistance, muscular endurance which is an ability of a muscle to repeatedly perform a number of contractions or relaxations against a given load over an extended period of time, and agility which is an ability of muscle to exert a potent force in a short time. Such muscular function is controlled by the liver, and is proportional to the muscle mass. The term 'improving muscular function' refers to making the muscular function better.

A composition for preventing, alleviating or treating muscle diseases or improving muscular function according to the present invention may contain Sargassum fulvellum, a Sargassum fulvellum dried powder, a Sargassum fulvellum extract or Sargassum fusiforme, a Sargassum fusiforme dried powder or a Sargassum fusiforme extract alone, may contain Sargassum fulvellum, a Sargassum fulvellum dried powder or a Sargassum fulvellum extract and Sargassum fusiforme, a Sargassum fusiforme dried powder or a Sargassum fusiforme extract at a mixed ratio of 1 to 100, or may also contain one or more active ingredients having functions similar to the aforementioned components. When the composition of the present invention includes an additional component, the composition may have a further enhanced effect of improving muscular function. The skin safety according to the components used together, ease in formulation, and stability of active ingredients may be contemplated upon addition of the component(s).

The present invention provides a pharmaceutical composition for preventing or treating muscle diseases; a health functional food composition for preventing or alleviating muscle diseases; a cosmetic composition for improving muscular function; and a feed additive for preventing or alleviating muscle diseases, each of which includes Sargassum fulvellum, a Sargassum fulvellum dried powder, a Sargassum fulvellum extract, Sargassum fusiforme, a Sargassum fusiforme dried powder or a Sargassum fusiforme extract as an active ingredient.

The present invention also provides a pharmaceutical composition for preventing or treating muscle diseases; a health functional food composition for preventing or alleviating muscle diseases; a cosmetic composition for improving muscular function; and a feed additive for preventing or alleviating muscle diseases, each of which includes a compound represented by Formula 1 or a Sargassum fulvellum or Sargassum fusiforme extract including the same as an active ingredient:

[Formula 1]

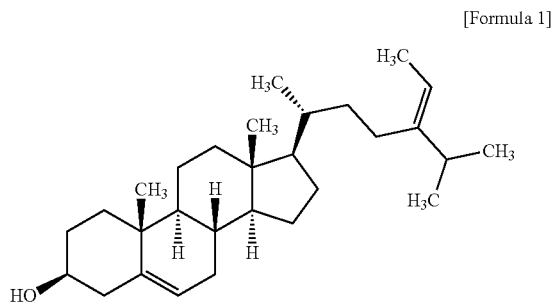

The compound of Formula 1 is also known as fucosterol.

The compound of Formula 1 may be isolated or synthesized from a marine alga and a plant extract or a fraction thereof, and used, or a commercially available compound may be used as the compound of Formula 1.

According to one exemplary embodiment, the fucosterol represented by Formula 1 may be fucosterol isolated from a Sargassum fulvellum extract or a Sargassum fusiforme extract.

According to one exemplary embodiment, the Sargassum fulvellum extract may be an ethanol extract, a hot water extract, a hexane extract, an ethyl acetate extract, an ultra-high pressure extract, a supercritical fluid extract, or a subcritical fluid extract, but the present invention is not limited thereto.

According to one exemplary embodiment, the Sargassum fulvellum extract may be obtained by extracting Sargassum

*fulvellum* with one or more solvents selected from the group consisting of water, an organic solvent having 1 to 6 carbon atoms, a subcritical fluid, and a supercritical fluid. For example, the *Sargassum fulvellum* extract may also be obtained by extracting *Sargassum fulvellum* under a condition of an ultra-high pressure of 100 MPa or more, preferably an ultra-high pressure of 100 MPa to 1,000 MPa. When necessary, the *Sargassum fulvellum* extract may be prepared by additional introduction of filtration and concentration processes according to the methods known in the related art.

According to one exemplary embodiment, the organic solvent having 1 to 6 carbon atoms may include one or more selected from the group consisting of an alcohol having 1 to 6 carbon atoms, acetone, ether, benzene, chloroform, ethyl acetate, methylene chloride, hexane, cyclohexane, and petroleum ether.

Also, the *Sargassum fulvellum* extract of the present invention may be obtained by extracting dried *Sargassum fulvellum* with purified water suitable for food processing, ethanol, and subcritical water or supercritical carbon dioxide and purifying the extracted *Sargassum fulvellum*, may be obtained by extracting dried *Sargassum fulvellum* using an ultra-high pressure extraction apparatus and purifying the extracted *Sargassum fulvellum*, or may be obtained by isolating and purifying an oil obtained by directly pressing *Sargassum fulvellum*. For example, the extract may be obtained by extracting *Sargassum fulvellum* under a condition of an ultra-high pressure of 100 MPa or more, preferably an ultra-high pressure of 100 MPa to 1,000 MPa.

According to one exemplary embodiment, the *Sargassum fusiforme* extract may be an ethanol extract, a hot water extract, a hexane extract, an ethyl acetate extract, an ultra-high pressure extract, a supercritical fluid extract, or a subcritical fluid extract, but the present invention is not limited thereto.

According to one exemplary embodiment, the *Sargassum fusiforme* extract may be obtained by extracting *Sargassum fusiforme* with one or more solvents selected from the group consisting of water, an organic solvent having 1 to 6 carbon atoms, a subcritical fluid, and a supercritical fluid. For example, the *Sargassum fusiforme* extract may be obtained by extracting *Sargassum fusiforme* under a condition of an ultra-high pressure of 100 MPa or more, preferably an ultra-high pressure of 100 MPa to 1,000 MPa. When necessary, the *Sargassum fusiforme* extract may be prepared by additional introduction of filtration and concentration processes according to the methods known in the related art.

According to one exemplary embodiment, the organic solvent having 1 to 6 carbon atoms may include one or more selected from the group consisting of an alcohol having 1 to 6 carbon atoms, acetone, ether, benzene, chloroform, ethyl acetate, methylene chloride, hexane, cyclohexane, and petroleum ether.

Also, the *Sargassum fusiforme* extract of the present invention may be obtained by extracting dried *Sargassum fusiforme* with purified water suitable for food processing, ethanol, and subcritical water or supercritical carbon dioxide and purifying the extracted *Sargassum fusiforme*, may be obtained by extracting dried *Sargassum fusiforme* using an ultra-high pressure extraction apparatus and purifying the extracted *Sargassum fusiforme*, or may be obtained by isolating and purifying an oil obtained by directly pressing *Sargassum fusiforme*. For example, the *Sargassum fusiforme* extract may be obtained by extracting *Sargassum fusiforme* under a condition of an ultra-high pressure of 100 MPa or more, preferably an ultra-high pressure of 100 MPa to 1,000 MPa.

According to one specific embodiment of the present invention, the present inventors have prepared an extract by repeatedly extracting dried *Sargassum fulvellum* or a *Sargassum fusiforme* dried powder at room temperature using methanol, ethanol, ethyl acetate and hexane as the solvent, or by performing hot water extraction, ultra-high pressure extraction, supercritical fluid extraction, subcritical fluid extraction, and the like.

Figure 2:
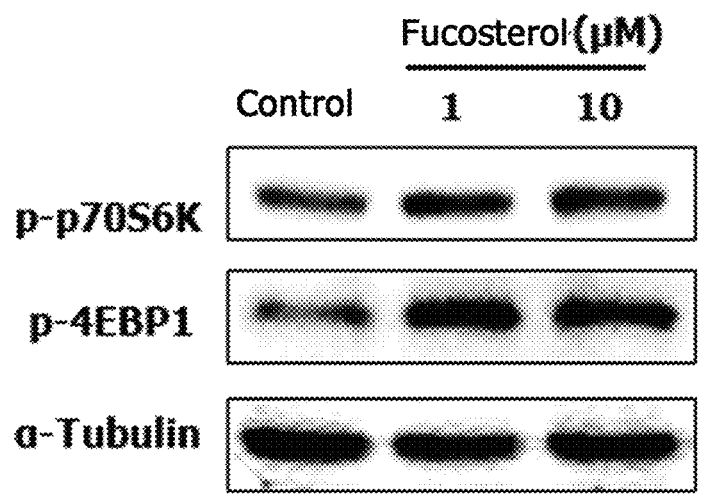
FIG. 2 shows results of measuring the protein expression of p-4EBP1 and p-p70S6K in L6 muscle cells when the L6 muscle cells are treated with fucosterol.
Figure 6:
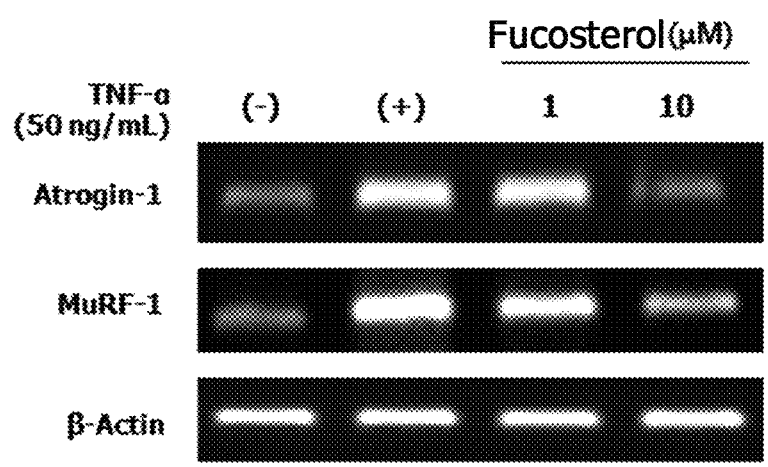
FIG. 6 shows results of measuring the mRNA expression of atrogin-1 and MuRF-1 in L6 muscle cells when the L6 muscle cells are treated with fucosterol.
Figure 7:
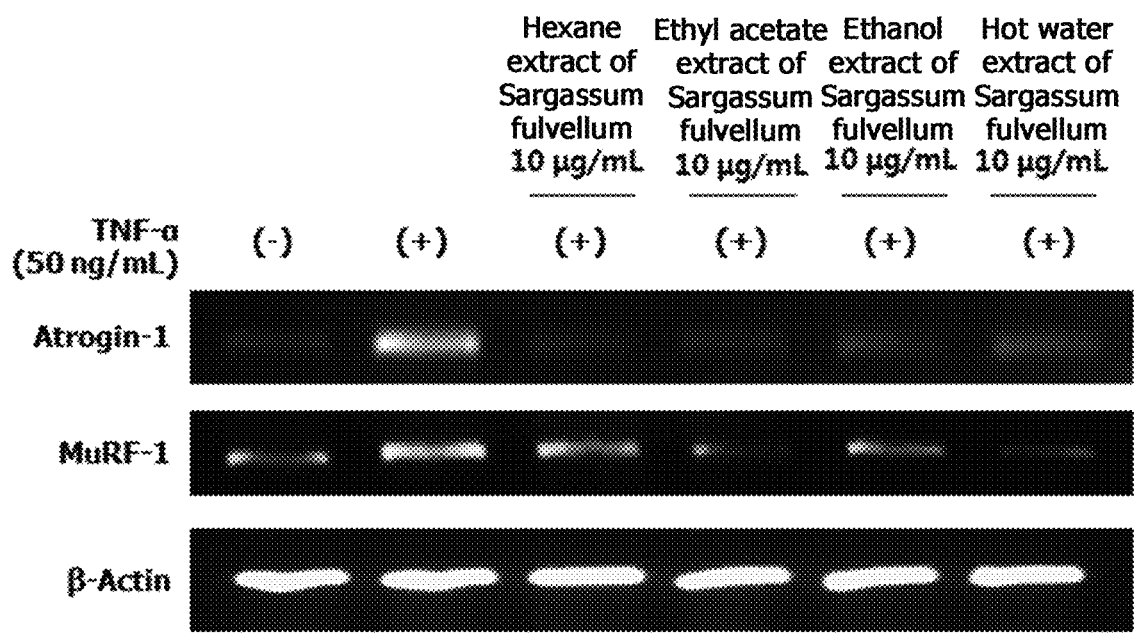
FIG. 7 shows results of measuring the mRNA expression of atrogin-1 and MuRF-1 in L6 muscle cells when the L6 muscle cells are treated with a hexane extract, an ethyl acetate extract, an ethanol extract, and a hot water extract of *Sargassum fulvellum*.
Figure 8:
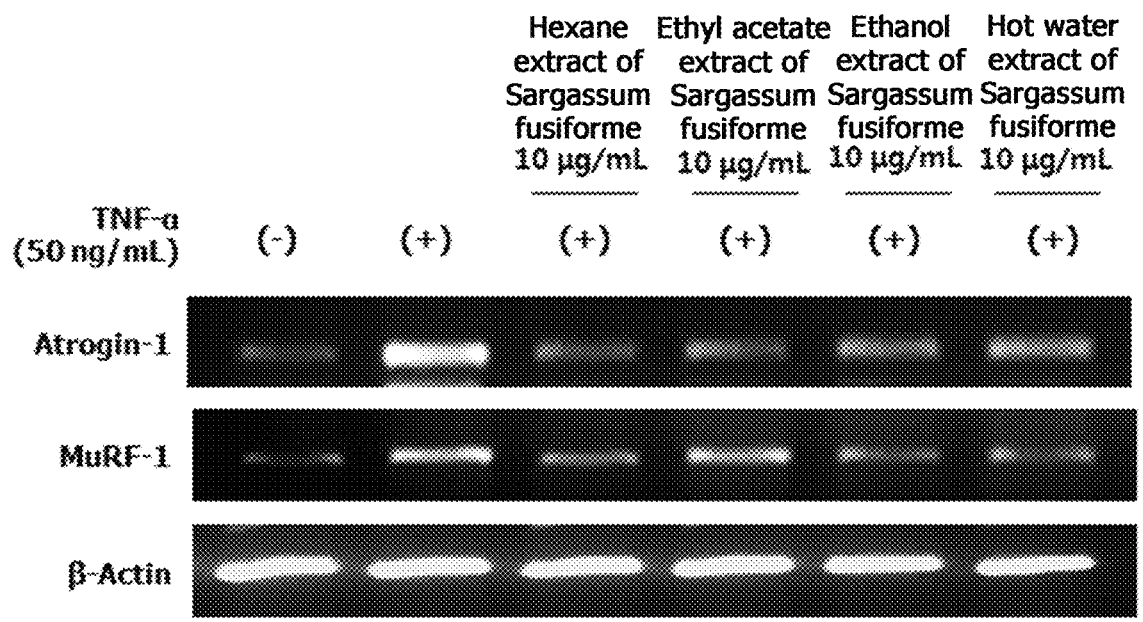
FIG. 8 shows results of measuring the mRNA expression of atrogin-1 and MuRF-1 in L6 muscle cells when the L6 muscle cells are treated with a hexane extract, an ethyl acetate extract, an ethanol extract, and a hot water extract of *Sargassum fusiforme*.

L6 muscle cells were treated with each of the ethanol extract of *Sargassum fulvellum*, the ethanol extract of *Sargassum fusiforme*, and fucosterol thus prepared to check the activity of the extracts and fucosterol in muscle cells. As a result, it was confirmed that the protein expression of p-mTOR involved in muscle protein synthesis increased (FIG. 1). Also, it was confirmed that the protein expression of p-4EBP1 and p-p70S6K involved in an mRNA translation process increased in L6 muscle cells when the L6 muscle cells were treated with fucosterol (FIG. 2). In addition, each of the fucosterol, and the hexane extract, ethyl acetate extract, ethanol extract and hot water extract of *Sargassum fulvellum* or *Sargassum fusiforme* increased the mRNA expression of MyoD and myogenin involved in muscle differentiation in L6 muscle cells (FIGS. 3 to 5), and inhibited the mRNA expression of MuRF-1 and atrogin-1 involved in muscle protein degradation (FIGS. 6 to 8).

In addition, the L6 muscle cells were treated with a high-pressure extract of *Sargassum fulvellum* or *Sargassum fusiforme* to check muscle development activity. As listed in Table 1, it was confirmed that each of an ultra-high pressure extract of *Sargassum fulvellum*, a supercritical fluid extract of *Sargassum fulvellum*, a subcritical fluid extract of *Sargassum fulvellum*, an ultra-high pressure extract of *Sargassum fusiforme*, a supercritical fluid extract of *Sargassum fusiforme*, and a subcritical fluid extract of *Sargassum fusiforme* increases a protein expression level of p-mTOR which is a main gene involved in muscular function improvement (Table 1). A change in weight of a muscle when a dried powder of *Sargassum fulvellum*, an ethanol extract of *Sargassum fulvellum*, a dried powder of *Sargassum fusiforme*, an ethanol extract of *Sargassum fusiforme*, or fucosterol was administered to a rat animal model in which muscle atrophy had been induced with TNF-α was measured. As a result, it was confirmed that the muscle mass significantly increases in all the respective treated groups, compared to the control (Table 2).

From the aforementioned results, because the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract according to the present invention, or the fucosterol isolated from the extracts exhibits an excellent effect in enhancing muscle mass, the *Sargassum fulvellum*, the *Sargassum fulvellum* dried powder, the *Sargassum fulvellum* extract, the *Sargassum fusiforme*, the *Sargassum fusiforme* dried powder, the *Sargassum fusiforme* extract, or the fucosterol may be effectively used in a pharmaceutical composition for preventing or treating muscle diseases; a health functional food composition for preventing or alleviating muscle diseases; a feed additive for preventing or alleviating muscle diseases; a cosmetic composition for improving muscular function; and a feed additive, or may be used as an active ingredient of a feed additive including the same.

When the composition for preventing or treating muscle diseases according to the present invention is a pharmaceutical composition, the composition may be used to prevent or treat muscle diseases caused by muscle wasting or degeneration. The muscle wasting and degeneration are caused by factors such as genetic factors, acquired factors, aging, and the like, and the muscle wasting is characterized by the gradual loss of muscle mass, and the weakening and regression of muscles, particularly skeletal or voluntary muscles and heart muscle. Examples of diseases associated with the muscle wasting and degeneration may include atony, muscular atrophy, muscular dystrophy, muscular degeneration, myasthenia, cachexia, and sarcopenia, but the present invention is not limited thereto. The composition of the present invention has an effect of increasing muscle mass, and types of the muscles are not limited.

The pharmaceutical composition of the present invention may include a pharmaceutically acceptable salt of the fucosterol, the *Sargassum fulvellum*, the *Sargassum fulvellum* dried powder, the *Sargassum fulvellum* extract, the *Sargassum fusiforme*, the *Sargassum fusiforme* dried powder, or the *Sargassum fusiforme* extract. In this specification, the term "pharmaceutically acceptable" generally means that a salt is physiologically acceptable, and usually does not cause an allergic reaction or similar reactions when administered to humans. In this case, an acid addition salt formed by a pharmaceutically acceptable free acid is desirable as the salt.

The pharmaceutically acceptable salt of the fucosterol, the *Sargassum fulvellum*, the *Sargassum fulvellum* dried powder, the *Sargassum fulvellum* extract, the *Sargassum fusiforme*, the *Sargassum fusiforme* dried powder, or the *Sargassum fusiforme* extract may be an acid addition salt formed using an organic acid or an inorganic acid. Examples of the organic acid includes, for example, formic acid, acetic acid, propionic acid, lactic acid, butyric acid, isobutyric acid, trifluoroacetic acid, malic acid, maleic acid, malonic acid, fumaric acid, succinic acid, monoamide succinate, glutamic acid, tartaric acid, oxalic acid, citric acid, glycolic acid, gluconic acid, ascorbic acid, benzoic acid, phthalic acid, salicylic acid, anthranilic acid, dichloroacetic acid, aminooxy acetic acid, benzene sulfonic acid, p-toluene sulfonic acid, or methanesulfonic acid. Examples of the inorganic acid include, for example, hydrochloric acid, bromic acid, sulfuric acid, phosphoric acid, nitric acid, carbonic acid, or boric acid. The acid addition salt may be preferably in the form of a hydrochloride or acetate, more preferably in the form of a hydrochloride.

The aforementioned acid addition salt is prepared using a method of preparing a conventional salt, which includes a) directly mixing fucosterol, *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract with an acid, or b) dissolving one component of the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract in a solvent or a functional solvent and mixing, or c) positioning fucosterol, *Sargassum fulvellum*, a *Sargassum fulvellum* dried powder, a *Sargassum fulvellum* extract, *Sargassum fusiforme*, a *Sargassum fusiforme* dried powder, or a *Sargassum fusiforme* extract in an acid in a solvent or a hydrated solvent and mixing.

In addition to the aforementioned salts, an additionally possible form of a salt includes GABA salts, pregabalin salts, nicotinates, adipates, hemimalonates, cysteine salts, acetylcysteine salts, methionine salts, arginine salts, lysine salts, ornithine salts, or aspartates.

Also, the pharmaceutical composition for preventing or treating muscle diseases according to the present invention may further include a pharmaceutically acceptable carrier.

The pharmaceutical composition may, for example, further include a carrier for oral administration or a carrier for parenteral administration as the pharmaceutically acceptable carrier. The carrier for oral administration may include lactose, starch, cellulose derivatives, magnesium stearate, stearic acid, and the like. Also, the carrier for parenteral administration may include water, suitable oils, saline, aqueous glucose, and glycol. In addition, the carrier for oral administration may further include a stabilizing agent and a preservative. A suitable stabilizing agent includes antioxidants such as sodium hydrogen sulfite, sodium bisulfite or ascorbic acid. A suitable preservative includes benzalkonium chloride, methyl- or propyl-paraben, and chlorobutanol. For other pharmaceutically acceptable carriers, refer to the carriers disclosed in the following document (Remington's Pharmaceutical Sciences, 19th ed., Mack Publishing Company, Easton, Pa., 1995).

The pharmaceutical composition of the present invention may be administered to a mammal including a human using any method. For example, the pharmaceutical composition may be orally or parenterally administered. In this case, a parenteral administration method may include intravenous, intramuscular, intra-arterial, intramedullary, intradural, intracardiac, percutaneous, subcutaneous, intraperitoneal, intranasal, intestinal, local, sublingual or intrarectal administration, but the present invention is not limited thereto.

The pharmaceutical composition of the present invention may be formulated into preparations for oral or parenteral administration, depending on the route of administration as described above. When formulated, the pharmaceutical composition may be prepared using one or more buffers (for example, saline or PBS), antioxidants, bacteriostatic agents, chelating agents (for example, EDTA or glutathione), fillers, extending agents, binders, adjuvants (for example, aluminum hydroxide), suspending agents, thickening agents, wetting agents, disintegrating agents or surfactants, diluents or excipients.

Also, a solid preparation for administration includes a tablet, a pill, a powder, a granule, a solution, a gel, a syrup, a slurry, a suspension, or a capsule. Such a solid preparation may be prepared by mixing one or more excipients, for example, starch (including corn starch, wheat starch, rice starch, potato starch, and the like), calcium carbonate, sucrose, lactose, dextrose, sorbitol, mannitol, xylitol, erythritol, maltitol, cellulose, methyl cellulose, sodium carboxymethyl cellulose and hydroxypropylmethyl-cellulose or gelatin, with the pharmaceutical composition of the present invention. For example, a tablet or a sugar-coated tablet may be obtained by blending the active ingredient with a solid excipient, grinding the resulting mixture, adding a suitable adjuvant thereto, and processing the mixture into granular mixtures.

Lubricants such as magnesium stearate, talc and the like are used in addition to the simple excipients. A liquid preparation for oral administration includes a suspending agent, a preparation for internal use, an emulsion or a syrup. In this case, the liquid preparation for oral administration may include various excipients, for example, a wetting agent, a sweetening agent, a flavoring agent, a preservative, and the like in addition to the generally used simple diluent such as water or liquid paraffin.

Also, cross-linked polyvinyl pyrrolidone, agar, alginic acid or sodium alginate, and the like may be added as a disintegrating agent, when necessary. Further, the pharmaceutical composition may further include an anti-agglomerating agent, a lubricant, a wetting agent, a flavoring agent, an emulsifying agent, a preservative, and the like.

When parenterally administered, the pharmaceutical composition of the present invention may be formulated with a suitable carrier for parenteral administration into the form of an injectable solution, a percutaneous administration preparation, and a nasal inhaler preparation using methods known in the related art. The injectable solution should be essentially sterilized, and protected from being contaminated by microbes such as bacteria and fungi. In the case of the injectable solution, examples of the suitable carrier may include a solvent or a dispersive medium such as water, ethanol, polyols (for example, glycerol, propylene glycol, liquid polyethylene glycol, and the like), a mixture thereof and/or vegetable oil, but the present invention is not limited thereto. More preferably, Hanks' solution, Ringer's solution, triethanolamine-containing phosphate-buffered saline (PBS) or sterile water for injections, or an isotonic solution such as 10% ethanol, 40% propylene glycol, and 5% dextrose may be used as the suitable carrier. The injectable solution may further include various antimicrobial and antifungal agents such as paraben, chlorobutanol, phenol, sorbic acid, thimerosal, and the like so as to protect the injectable solution from being contaminated by microbes. In most cases, the injectable solution may also further include an isotonic agent such as a sugar or sodium chloride.

The percutaneous administration preparation is included in the form of an ointment, a cream, a lotion, a gel, a preparation for external use on skin, a paste, a liniment, an aerosol, and the like. As such, the term "percutaneous administration" means that an effective amount of the active ingredient included in the pharmaceutical composition is delivered into the skin when the pharmaceutical composition is locally administered to the skin.

In the case of an inhaling administration preparation, the compound used according to the present invention may be readily delivered in the form of an aerosol spray from a pressurized pack or a sprayer using a suitable propellant, for example, dichlorofluoromethane, trichlorofluoromethane, dichlorotetrafluoroethane, carbon dioxide, or other suitable gases. The dosage of pressured aerosol may be determined by providing a valve through which an amount of calculated aerosol passes. For example, a gelatin capsule and a cartridge used in a nebulizer or an insufflator may be formulated to contain a powder mixture of a compound and a suitable powder base such as lactose or starch. Formulations for parenteral administration are disclosed in the document (Remington's Pharmaceutical Science, 15th Edition, 1975. Mack Publishing Company, Easton, Pa. 18042, Chapter 87: Blaug, Seymour), which is a commonly known formulary for all pharmaceutical chemistries.

The pharmaceutical composition for preventing or treating muscle diseases according to the present invention may provide a desirable effect of preventing or treating muscle diseases when the pharmaceutical composition includes an effective amount of fucosterol, *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract. In this specification, 'effective amount' refers to an amount sufficient to cause a higher reaction compared to the negative control, preferably an amount sufficient to improve the muscular function. The pharmaceutical composition of the present invention may include the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract at an amount of 0.01 to 99.99%, and a pharmaceutically acceptable carrier may account for the rest. The effective amount of the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract included in the pharmaceutical composition of the present invention may vary depending on the form into which the composition is manufactured, and the like.

The total effective amount of the pharmaceutical composition of the present invention may be administered to patients in a single dose, and may be administered according to the fractionated treatment protocol in which multiple doses are administered for a long period of time. The pharmaceutical composition of the present invention may include a varying content of the active ingredient, depending on the severity of a disease. When parenterally administered, the pharmaceutical composition may be administered once or several divided times so that the daily dose of the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract is preferably in a range of 0.01 to 50 mg, more preferably 0.1 to 30 mg, based on 1 kg of body weight. When orally administered, the pharmaceutical composition may also be administered once or several divided times so that the daily dose of the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract is preferably in a range of 0.01 to 100 mg, more preferably 0.01 to 10 mg, based on 1 kg of body weight. However, the effective dose of the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract may be determined in consideration of various factors such as the age, weight, health condition and sex of a patient, the severity of a disease, diet, and secretion rate as well as a route of administration of the pharmaceutical composition and the number of treatments. Therefore, when considering these factors, a person having ordinary skill in the related art may easily determine a suitable effective dose of the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract for the specific purpose of preventing or treating muscle diseases. The formulation, the route of administration and the administration method are not particularly limited as long as the pharmaceutical composition according to the present invention exhibits the effects of the present invention.

The pharmaceutical composition for preventing or treating muscle diseases according to the present invention may be used with or without surgery, radiotherapy, hormone therapy, chemotherapy, and methods using a biological response modifier.

The pharmaceutical composition for preventing or treating muscle diseases according to the present invention may be provided as a formulation for preparation for external use on skin, which includes the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract as the active ingredient.

When the pharmaceutical composition for preventing or treating muscle diseases according to the present invention is used as a preparation for external use on skin, the pharmaceutical composition may further contain adjuvants generally used in the field of dermatology, such as any other components generally used in the preparation for external use on skin, for example, a fatty material, an organic solvent, a dissolving agent, concentrating and gelling agents, a softening agent, an antioxidant, a suspending agent, a stabilizing agent, a foaming agent, a flavoring agent, a surfactant, water, an ionic emulsifying agent, a non-ionic emulsifying agent, a filler, a sequestering agent, a chelating agent, a preservative, a vitamin, a blocking agent, a wetting agent, an essential oil, a dye, a pigment, a hydrophilic activating agent, a hydrophobic activating agent, or a lipid vesicle. Also, the components may be introduced at an amount generally used in the field of dermatology.

When the pharmaceutical composition for preventing or treating muscle diseases according to the present invention is provided as the preparation for external use on skin, the pharmaceutical composition may be a formulation such as an ointment, a patch, a gel, a cream or a spray, but the present invention is not limited thereto.

The composition for preventing muscle diseases or improving muscular function according to the present invention may also be a food composition. When the composition for preventing muscle diseases or improving muscular function according to the present invention is the food composition, the composition may be used to prevent and alleviate muscle diseases caused by muscle wasting or degeneration. The muscle wasting and degeneration are caused by factors such as genetic factors, acquired factors, aging, and the like, and the muscle wasting is characterized by the gradual loss of muscle mass, and the weakening and regression of muscles, particularly skeletal or voluntary muscles and heart muscle. Examples of diseases associated with the muscle wasting and degeneration may include atony, muscular atrophy, muscular dystrophy, muscular degeneration, myasthenia, cachexia, and sarcopenia. The composition of the present invention has an effect of increasing muscle mass, and types of the muscles are not limited.

The food composition of the present invention includes all types of a functional food, a nutritional supplement, a health food, a food additive, feed, and the like, and fed to animals including humans or livestock. The types of the food composition may be prepared in various forms according to conventional methods known in the related art.

The types of the food composition may be prepared in various forms according to conventional methods known in the related art. Common foods may be prepared by adding the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract to beverages (including alcoholic beverages), fruits and processed foods thereof (e.g., canned fruits, bottled fruits, jam, marmalade, and the like), fish, meat and processed foods thereof (e.g., ham, sausage, corn beef, and the like), bread and noodles (e.g., udon, buckwheat noodles, ramen, spaghetti, macaroni, and the like), fruit juices, various drinks, cookies, taffy, dairy products (e.g., butter, cheese, and the like), edible vegetative oils, margarine, vegetable proteins, retort foods, frozen foods, various condiments (e.g., soybean paste, soy sauce, sauces, and the like), and the like, but the present invention is not limited thereto. Also, the nutritional supplement may be prepared by adding the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract to capsules, tablets, pills, and the like, but the present invention is not limited thereto. In addition, the health functional food may, for example, be prepared into liquids, granules, capsules and powders so that the *Sargassum fulvellum* extract or *Sargassum fusiforme* extract itself can be prepared in the form of teas, juices and drinks so as to ingest health drinks, but the present invention is not limited thereto. To use the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract in the form of a food additive, the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract may also be prepared in the form of a powder or a concentrate, and used. Further, the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract may be prepared in the form of a composition by being mixed with active ingredients known to have an effect of preventing muscle diseases or improving muscular function.

When the composition for preventing muscle diseases or improving muscular function according to the present invention is used as the health drink composition, the health drink composition may further contain additional components such as various flavoring agents or natural carbohydrates as in conventional drinks. The aforementioned natural carbohydrates may include monosaccharides such as glucose, fructose, and the like; disaccharides such as maltose, sucrose, and the like; polysaccharides such as dextrin, cyclodextrin, and the like; and sugar alcohols such as xylitol, sorbitol, erythritol, and the like. Natural sweetening agents such as thaumatin, a *stevia* extract, and the like; synthetic sweetening agents such as saccharin, aspartame, and the like may be used as the sweetening agent. A ratio of the natural carbohydrate is generally in a range of approximately 0.01 to 0.04 g, preferably approximately 0.02 to 0.03 g per 100 mL of the composition of the present invention.

The fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract may be included as the active ingredient of the food composition for preventing or alleviating muscle diseases. In this case, an amount of the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract refers to an amount effective for achieving the effect of preventing muscle diseases or improving muscular function, but the present invention is not particularly limited thereto. For example, the amount is preferably in a range of 0.01 to 100% by weight, based on the total weight of the composition. The food composition of the present invention may be prepared by mixing the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract with other active ingredients known to be effective in the composition for preventing muscle diseases or improving muscular function.

In addition to the aforementioned components, the health food of the present invention may contain various nutrients, vitamins, electrolytes, a flavoring agent, a coloring agent, pectic acid, a pectate, alginic acid, an alginate, organic acids, a protective colloidal thickening agent, a pH control agent, a stabilizing agent, a preservative, glycerin, an alcohol, or a carbonating agent. In addition, the health food of the present invention may include pulp for preparing a natural fruit juice, a fruit juice drink or a vegetable drink. Such components may be used alone or in combination. The ratio of such additives is not important, but the additives are generally chosen in a range of 0.01 to 0.1 parts by weight, based on 100 parts by weight of the composition of the present invention.

The composition for improving muscular function according to the present invention may also be a cosmetic composition. The cosmetic composition of the present invention includes the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract as the active ingredient, and may be prepared together with a dermatologically acceptable excipient in the form of a fundamental cosmetic composition (a toner, a cream, a nourishing serum, a facial cleanser (i.e., a cleansing foam and a cleansing water), a pack, or a body oil), a color cosmetic composition (a foundation, a lipstick, mascara, or a make-up base), a hair product composition (a shampoo, a rinse, a hair conditioner, or a hair gel), and soap.

The excipient may, for example, include a skin softening agent, a skin penetration enhancing agent, a coloring agent, a flavoring agent, an emulsifying agent, a thickening agent, and a solvent, but the present invention is not limited thereto. Also, the excipient may further include a flavoring agent, a pigment, a disinfectant, an antioxidant, a preservative, and a moisturizing agent, and may include a thickening agent, inorganic salts, synthetic polymeric materials, and the like for the purpose of improving physical properties. For example, when the cosmetic composition of the present invention is prepared into a facial cleanser and soap, the facial cleanser and soap may be easily prepared by adding the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract to conventional facial cleansers and soap bases. When the cosmetic composition of the present invention is prepared into a cream, the cream may be prepared by adding the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract or salts thereof to conventional oil-in-water (O/W) cream bases. A flavoring agent, a chelating agent, a pigment, an antioxidant, a preservative, and synthetic or natural substances (for example, proteins, minerals, vitamins, and the like) used to improve physical properties may be additionally added to the cream.

A content of the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract included in the cosmetic composition of the present invention is preferably in a range of 0.001 to 10% by weight, more preferably in a range of 0.01 to 5% by weight, based on the total weight of the composition, but the present invention is not limited thereto. When the content is less than 0.001% by weight, it is impossible to expect a desired effect of improving muscular function. On the other hand, when the content is greater than 10% by weight, safety-related problems or difficulty in preparing formulations may occur.

The composition of the present invention may be added to a feed additive or a feed composition including the same for the purpose of preventing or alleviating muscle diseases.

In the present invention, the term "feed additive" refers to substances added to feed for the purpose of various effects of supplementing nutrients and preventing weight loss, promoting digestibility of cellulose in feed, improving oil quality, preventing reproductive disorders and improving a rate of pregnancy, preventing high-temperature stress during the summer season, and the like. The feed additive of the present invention belongs to supplementary feed according to the Control of Livestock and Fish Feed Act, and may further include mineral preparations such as sodium hydrogen carbonate, bentonite, magnesium oxide, complex minerals, and the like, mineral preparations such as trace minerals, for example, zinc, copper, cobalt, selenium, and the like, vitamin preparations such as carotene, vitamins A, D, and E, nicotinic acid, vitamin B complexes, protective amino acid powders such as methionine, lysine, and the like, protective fat powders such as fatty acid calcium salt, and the like, living microbes such as probiotics (lactic acid bacteria), yeast cultures, fungal fermentation products, yeast preparations, and the like.

In the present invention, the term "feed" refers to any natural or artificial diet, a single meal, or the like, or a component of the single meal, which an animal eats, ingests and digests or which is suitable for eating, ingestion and digestion. In this case, the feed including the composition for preventing or alleviating muscle diseases according to the present invention as the active ingredient may be prepared into various forms of feed known in the related art, and may preferably include concentrated feed, crude feed and/or specialty feed, but the present invention is not limited thereto.

The concentrated feed includes seeds and fruits including crops such as wheat, oats, corn, and the like; bran including rice bran, wheat bran, barley bran, and the like as by-products obtained by refining crops; oil cakes such as by-products obtained by extracting oil from beans, rapeseed, sesame, linseed, coconut palms, and the like; dregs such as starch residues that are main components of starch pulp remaining after starch is extracted from sweet potatoes, potatoes, and the like; animal feed such as fish meal, fish scraps, fish soluble obtained by concentrating a fresh liquid product obtained from fish, meat meal, blood meal, feather meal, skimmed milk powder, dried whey obtained by drying whey which is a solution remaining when cheese and casein are prepared from milk and skim milk, respectively; and yeast, *chlorella*, and marine algae, but the present invention is not limited thereto.

The crude feed includes fresh herbal feed such as wild grass, grass, fodder, and the like; root vegetables such as turnips for feed, beets for feed, rutabaga which is a type of turnip; silage which is storage feed prepared by lactic-acid-fermentation of green forage, fodder crops, and grain filled in a silo; hay prepared by cutting and drying wild grass and grass; straw of crops for breeding stock; and leaves of beans and plants, but the present invention is not limited thereto. The specialty feed includes mineral feed such as oyster shells and rock salt; urea feed including urea or derivatives thereof such as isobutane diureide; and feed additives or dietary supplements which are added in a trace amount to assorted feeds so as to supplement components which are lacking when only natural ingredients are blended or to improve storability of the feeds, but the present invention is not limited thereto.

The feed additive for preventing or alleviating muscle diseases according to the present invention may be prepared by adding the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract in a suitable effective concentration range according to various methods of preparing feed known in the related art.

The feed additive according to the present invention may be applied without limitation as long as the feed additive is applied to a subject for the purpose of preventing or alleviating muscle diseases. For example, the feed additive may be applied to any subject including non-human animals such as a monkey, a dog, a cat, a rabbit, a guinea pig, a rat, a mouse, a cow, sheep, a pig, and a goat; birds; and fish.

EXAMPLES

Hereinafter, the present invention will be described in detail with reference to examples thereof.

However, it should be understood that the following examples are just preferred examples for the purpose of illustration only and are not intended to limit or define the scope of the present invention.

Reference Example 1: Material Information on Fucosterol

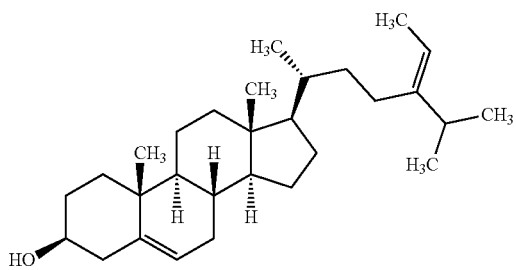

Name: Fucosterol; (24E)-24-N-Propylidenecholesterol; 24-Isoethylidenecholest-5-en-3beta-ol, delta-(5)-avenasterol; 28-Isofucosterol; Stigmasta-5,24-dien-3beta-ol; Stigmasta-5,24(28)-dien-3-ol; (3-beta,24E)-/(3-beta,24Z)-stigmasta-5,24(28)-dien-3-ol; (3-beta,24E)-stigmasta-5,24(28)-dien-3-ol; (24E)-stigmasta-5,24(28)-dien-3-ol CAS No.: 17605-67-3

Example 1

Preparation of *Sargassum fulvellum* Extract

<1-1> Preparation of Methanol Extract of *Sargassum fulvellum*

Dried *Sargassum fulvellum* was ground in a mixer, and 100 g of the ground *Sargassum fulvellum* sample was then added to 1 L of 100% methanol, and repeatedly extracted three times at room temperature for 24 hours. The extracted sample was filtered through Whatman grade 2 filter paper under reduced pressure, and the filtered extraction solution was concentrated in a rotary vacuum evaporator to remove solvent components, thereby obtaining a methanol extract of *Sargassum fulvellum*.

<1-2> Preparation of Ethanol Extract of *Sargassum fulvellum*

Dried *Sargassum fulvellum* was ground in a mixer, and 100 g of the ground *Sargassum fulvellum* sample was then added to 1 L of 100% ethanol, and repeatedly extracted three times at room temperature for 24 hours. The extracted sample was filtered through Whatman grade 2 filter paper under reduced pressure, and the filtered extraction solution was concentrated in a rotary vacuum evaporator to remove solvent components, thereby obtaining an ethanol extract of *Sargassum fulvellum*.

<1-3> Preparation of Ethyl Acetate Extract of *Sargassum fulvellum*

Dried *Sargassum fulvellum* was ground in a mixer, and 100 g of the ground *Sargassum fulvellum* sample was then added to 1 L of 100% ethyl acetate, and repeatedly extracted three times at room temperature for 24 hours. The extracted sample was filtered through Whatman grade 2 filter paper under reduced pressure, and the filtered extraction solution was concentrated in a rotary vacuum evaporator to remove solvent components, thereby obtaining an ethyl acetate extract of *Sargassum fulvellum*.

<1-4> Preparation of Hexane Extract of *Sargassum fulvellum*

Dried *Sargassum fulvellum* was ground in a mixer, and 100 g of the ground *Sargassum fulvellum* sample was then added to 1 L of 100% hexane, and repeatedly extracted three times at room temperature for 24 hours. The extracted sample was filtered through Whatman grade 2 filter paper under reduced pressure, and the filtered extraction solution was concentrated in a rotary vacuum evaporator to remove solvent components, thereby obtaining a hexane extract of *Sargassum fulvellum*.

<1-5> Preparation of Hot Water Extract of *Sargassum fulvellum*

Dried *Sargassum fulvellum* was ground in a mixer, and 100 g of the ground *Sargassum fulvellum* sample was then added to 1 L of water, and extracted while stirring at 80° C. for 2 hours. The extracted sample was filtered through Whatman grade 2 filter paper under reduced pressure, and the filtered extraction solution was concentrated in a rotary vacuum evaporator to remove solvent components, thereby obtaining a hot water extract of *Sargassum fulvellum*.

<1-6> Preparation of Ultra-High Pressure Extract of *Sargassum fulvellum*

Dried *Sargassum fulvellum* was ground in a mixer, and 1 g of the ground *Sargassum fulvellum* and 76 mL of 18% ethanol were then put into a polyethylene pack, which was then sealed. Thereafter, the resulting mixture was extracted using an ultra-high pressure extraction apparatus (Frescal MFP-7,000; Mitsubishi Heavy Industries). The ultra-high pressure extraction conditions were as follows: an extraction pressure was 320 MPa, and an extraction time was 5 minutes. The extracted sample was filtered through Whatman grade 2 filter paper, and the filtered extraction solution was concentrated in a rotary vacuum evaporator to remove solvent components, thereby obtaining an ultra-high pressure extract of *Sargassum fulvellum*.

<1-7> Preparation of Supercritical Fluid Extract of *Sargassum fulvellum*

Dried *Sargassum fulvellum* was ground in a mixer, and 1 g of the ground *Sargassum fulvellum* sample was then filled in a sample cartridge, and extracted using a supercritical fluid extraction apparatus (SFX 3560, Isco Inc., Lincoln, Nebr., USA). The supercritical fluid extraction conditions were as follows: an extraction pressure was 40 MPa, an extraction temperature was 50° C., a flow rate of supercritical carbon dioxide was 60 mL/min, and an extraction time was 60 minutes. When the supercritical fluid extraction was completed, a pressure of the extraction apparatus was reduced to release a supercritical fluid state, thereby obtaining a supercritical fluid extract of *Sargassum fulvellum*.

<1-8> Preparation of Subcritical Fluid Extract of *Sargassum fulvellum*

Dried *Sargassum fulvellum* was ground in a mixer, and 1 g of the ground *Sargassum fulvellum* sample was then added to 10 mL of distilled water, and extracted using a subcritical fluid extraction apparatus (DIONEX Accelerated Solvent Extractor 100, DIONEX Co., USA). The subcritical fluid extraction conditions were as follows: an extraction pressure of 2.5 MPa, an extraction temperature of 150° C., and an extraction time of 15 minutes. The extracted sample was filtered through Whatman grade 2 filter paper, and the filtered extraction solution was freeze-dried at −40° C. to obtain a subcritical fluid extract of *Sargassum fulvellum*.

Example 2

Preparation of *Sargassum fusiforme* Extract

<2-1> Preparation of Methanol Extract of *Sargassum fusiforme*

Dried *Sargassum fusiforme* was ground in a mixer, and 100 g of the ground *Sargassum fusiforme* sample was then added to 1 L of 100% methanol, and repeatedly extracted three times at room temperature for 24 hours. The extracted sample was filtered through Whatman grade 2 filter paper under reduced pressure, and the filtered extraction solution was concentrated in a rotary vacuum evaporator to remove solvent components, thereby obtaining a methanol extract of *Sargassum fusiforme*.

<2-2> Preparation of Ethanol Extract of *Sargassum fusiforme*

Dried *Sargassum fusiforme* was ground in a mixer, and 100 g of the ground *Sargassum fusiforme* sample was then added to 1 L of 100% ethanol, and repeatedly extracted three times at room temperature for 24 hours. The extracted sample was filtered through Whatman grade 2 filter paper under reduced pressure, and the filtered extraction solution was concentrated in a rotary vacuum evaporator to remove solvent components, thereby obtaining an ethanol extract of *Sargassum fusiforme*.

<2-3> Preparation of Ethyl Acetate Extract of *Sargassum fusiforme*

Dried *Sargassum fusiforme* was ground in a mixer, and 100 g of the ground *Sargassum fusiforme* sample was then added to 1 L of 100% ethyl acetate, and repeatedly extracted three times at room temperature for 24 hours. The extracted sample was filtered through Whatman grade 2 filter paper under reduced pressure, and the filtered extraction solution was concentrated in a rotary vacuum evaporator to remove solvent components, thereby obtaining an ethyl acetate extract of *Sargassum fusiforme*.

<2-4> Preparation of Hexane Extract of *Sargassum fusiforme*

Dried *Sargassum fusiforme* was ground in a mixer, and 100 g of the ground *Sargassum fusiforme* sample was then added to 1 L of 100% hexane, and repeatedly extracted three times at room temperature for 24 hours. The extracted sample was filtered through Whatman grade 2 filter paper under reduced pressure, and the filtered extraction solution was concentrated in a rotary vacuum evaporator to remove solvent components, thereby obtaining a hexane extract of *Sargassum fusiforme*.

<2-5> Preparation of Hot Water Extract of *Sargassum fusiforme*

Dried *Sargassum fusiforme* was ground in a mixer, and 100 g of the ground *Sargassum fusiforme* sample was then added to 1 L of water, and extracted while stirring at 80° C. for 2 hours. The extracted sample was filtered through Whatman grade 2 filter paper under reduced pressure, and the filtered extraction solution was concentrated in a rotary vacuum evaporator to remove solvent components, thereby obtaining a hot water extract of *Sargassum fusiforme*.

<2-6> Preparation of Ultra-High Pressure Extract of *Sargassum fusiforme*

Dried *Sargassum fusiforme* was ground in a mixer, and 1 g of the ground *Sargassum fusiforme* sample and 76 mL of 18% ethanol were put into a polyethylene pack, which was then sealed. Thereafter, the resulting mixture was extracted using an ultra-high pressure extraction apparatus (Frescal MFP-7,000; Mitsubishi Heavy Industries). The ultra-high pressure extraction conditions were as follows: an extraction pressure was 320 MPa, and an extraction time was 5 minutes. The extracted sample was filtered through Whatman grade 2 filter paper, and the filtered extraction solution was concentrated in a rotary vacuum evaporator to remove solvent components, thereby obtaining an ultra-high pressure extract of *Sargassum fusiforme*.

<2-7> Preparation of Supercritical Fluid Extract of *Sargassum fusiforme*

Dried *Sargassum fusiforme* was ground in a mixer, and 1 g of the ground *Sargassum fusiforme* sample was then filled in a sample cartridge, and extracted using a supercritical fluid extraction apparatus (SFX 3560, Isco Inc., Lincoln, Nebr., USA). The supercritical fluid extraction conditions were as follows: an extraction pressure was 40 MPa, an extraction temperature was 50° C., a flow rate of supercritical carbon dioxide was 60 mL/min, and an extraction time was 60 minutes. When the supercritical fluid extraction was completed, a pressure of the extraction apparatus was reduced to remove a supercritical fluid state, thereby obtaining a supercritical fluid extract of *Sargassum fusiforme*.

<2-8> Preparation of Subcritical Fluid Extract of *Sargassum fusiforme*

Dried *Sargassum fusiforme* was ground in a mixer, and 1 g of the ground *Sargassum fusiforme* sample was then added to 10 mL of distilled water, and extracted using a subcritical fluid extraction apparatus (DIONEX Accelerated Solvent Extractor 100, DIONEX Co., USA). The subcritical fluid extraction conditions were as follows: an extraction pressure of 2.5 MPa, an extraction temperature of 150° C., and an extraction time of 15 minutes. The extracted sample was filtered through Whatman grade 2 filter paper, and the filtered extraction solution was freeze-dried at −40 to obtain a subcritical fluid extract of *Sargassum fusiforme*.

Example 3

Isolation of Fucosterol 500 g of dried *Sargassum fulvellum* or *Sargassum fusiforme* was ground in a mixer, and added to 5 L of hexane. Thereafter, the resulting mixture was extracted at room temperature for 48 hours by cold maceration. The extracted sample was filtered through Whatman grade 2 filter paper, and the filtered extraction solution was concentrated in a rotary vacuum evaporator to remove solvent components, thereby obtaining approximately 15.0 g of a hexane extract. 15 g of the hexane-soluble extract was loaded on a silica gel open column (70-230 mesh, Merck&Co., Whitehouse Station, N.J., USA), and fractionated using a mixed solvent system of hexane and ethyl acetate. The resulting fractions fractionated in a concentration gradient were divided into 40 sub-fractions according to the fractionation order. Thereafter, fucosterol (210 mg) which was a compound represented by the following Formula 1 was isolated from the 10th to 30th fractions.

[Formula 1]

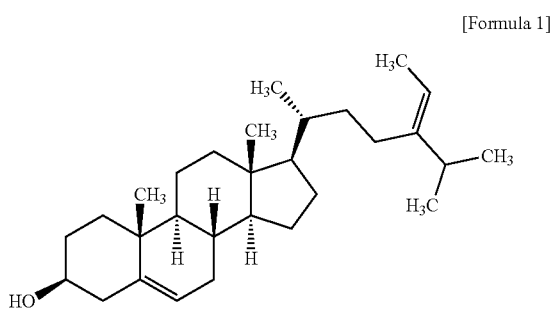

Example 4

Muscle Development Activity of Fucosterol, *Sargassum fulvellum* Extract or *Sargassum fusiforme* Extract As muscle cells, L6 myoblasts (ATCC CRL-1458, Manassas, Va., USA) were added to a 6-well plate at a density of $2 \times 10^5$ cells/mL together with a Dulbecco's modified Eagle's medium (DMEM; Hyclone) supplemented with 10% fetal bovine serum (FBS; Hyclone, Logan, Utah, USA). When the cell density reached approximately 80 to 85%, the medium contained in the wells was removed, and each of the ethanol extract of *Sargassum fulvellum* (20 μg/mL) prepared in Example 1-2, the ethanol extract of *Sargassum fusiforme* (20 μg/mL) prepared in Example 2-2, and the fucosterol (10 μM) isolated and purified in Example 3 was dissolved in DMEM (Hyclone) supplemented with 2% horse serum (HS; Hyclone), and cells were then treated with the resulting mixture to induce myotube differentiation. In this case, a group in which the cells were treated with 0.01% DMSO instead of the sample was used as the control. This procedure was carried out at an interval of 2 days for 6 days to differentiate the cells, and the cells were then dissolved in an NP-40 buffer (ELPIS-Biotech, Daejeon, Korea) containing a proteinase inhibitor cocktail. The cells lysed in the buffer were transferred to a 1.5 ml tube, and centrifuged at 13,000 rpm for 10 minutes to collect only a supernatant. The supernatant was quantified using a Bradford method (Bradford, Bio-Rad Laboratories Inc., Hercules, Calif., USA). The quantified proteins were boiled for 5 minutes, and separated through 10% SDS-PAGE, and the separated proteins were transferred to a nitrocellulose membrane. A p-mTOR primary antibody (Cell Signaling Technology, Beverly, Mass., USA) was diluted with 2.5% bovine serum albumin (BSA) at a ratio of 1:1,000, and reacted with the proteins transferred to the nitrocellulose membrane at room temperature for 20 hours. After the primary antibody reaction was completed, the nitrocellulose membrane was washed three times with Tris-buffer Saline Tween 20 (TBST) for 10 minutes. After the washing, a horseradish peroxidase-conjugated anti-rabbit secondary antibody (Bethyl Laboratories, Inc., Montgomery, Tenn., USA) recognizing the primary antibody was diluted with 2.5% BSA at a ratio of 1:5,000, and reacted with the nitrocellulose membrane at room temperature for 2 hours. Then, the nitrocellulose membrane was washed three times with TBST for 10 minutes. Protein bands were chromogenically developed using an ECL Western blotting detection reagent (Amersham, Tokyo, Japan), and the chromogenically developed protein bands were confirmed using a G;BOX EF imaging system (Syngene, Cambridge, UK). The results are shown in FIG. 1.

As a result, it can be seen that an expression level of p-mTOR increased in the L6 muscle cells when the L6 muscle cells were treated with the ethanol extract of *Sargassum fulvellum*, the ethanol extract of *Sargassum fusiforme*, and the fucosterol, as shown in FIG. 1. This indicates that the ethanol extract of *Sargassum fulvellum*, the ethanol extract of *Sargassum fusiforme*, and the fucosterol according to the present invention have an excellent ability of increasing muscle development in muscle cells.

Example 5 mRNA Translation-Promoting Activity of Fucosterol in L6 Muscle Cells

The fucosterol isolated and purified in Example 3 was tested at concentrations of 1 and 10 μM in the same manner as in Example 4. Proteins were treated with p-p70S6K and p-4EBP1 primary antibodies (Santa Cruz Biotechnology, Santa Cruz, Calif., USA), which were involved in an mRNA translation process, instead of the p-mTOR primary antibody so as to confirm protein bands.

As a result, it can be seen that protein expression levels of p-p70S6K and p-4EBP1 involved in the mRNA translation process increased in the L6 muscle cells when the L6 muscle cells were treated with the fucosterol, as shown in FIG. 2. This indicates that the fucosterol of the present invention promotes the mRNA translation process for muscle development in the muscle cells.

Example 6

Muscle Differentiation Activity of Fucosterol

As muscle cells, L6 myoblasts (ATCC) were added to a 6-well plate at a density of $2 \times 10^5$ cells/mL together with DMEM (Hyclone) supplemented with 10% FBS (Hyclone). When the cell density reached approximately 80 to 85%, the medium contained in the wells was removed, and the fucosterol isolated and purified in Example 3 was dissolved at concentrations of 1 and 10 μM in DMEM (Hyclone) supplemented with 2% HS (Hyclone), and the cells were treated with the fucosterol to induce myotube differentiation. In this case, a group in which the cells were treated with 0.01% DMSO instead of the sample was used as the control. This procedure was carried out at an interval of 2 days for 6 days to differentiate the cells, and total RNA was isolated using a TRIzol reagent (Invitrogen, Carlsbad, Calif., USA). The isolated total RNA was quantified using NanoDrop 1000 (Thermo Fisher Scientific Inc., MA, USA). 16 μL of the quantified RNA was synthesized into cDNA using Reverse Transcriptase Premix (ELPIS-Biotech) and a PCR machine (Gene Amp PCR System 2700, Applied Biosystems, MA, USA) under conditions of 42° C. and 55 minutes and 70° C. and 15 minutes. PCR was performed by repeating 30 cycles at 95° C. for 30 seconds, at 60° C. for 1 minute, and at 72° C. for 1 minute using 4 μL of cDNA (from 16 μL of the synthesized cDNA), the following specific primers (Bioneer, Daejeon, Korea), and a PCR premix (ELPIS-Biotech).

MyoD:

Forward primer: 5'-TTTCGACTCACCAGACCTGC-3' (SEQ ID NO: 1)

Reverse primer: 5'-CAGAGCCTGCAGACCTTCAA-3' (SEQ ID NO: 2)

Myogenin:

Forward primer: 5'-TTTCGCACCTGATGGACCTG-3' (SEQ ID NO: 3)

Reverse primer: 5'-CTTTCTTGAGCCTGCGCTTC-3' (SEQ ID NO: 4)

β-Actin:

Forward primer: 5'-AGCCATGTACGTAGCCATCC-3' (SEQ ID NO: 5)

Reverse primer: 5'-CTCTCAGCTGTGGTGCTGAA-3' (SEQ ID NO: 6)

The PCR-amplified cDNA was isolated by electrophoresis in a 1.5% agarose gel, and a cDNA band was confirmed using a G;BOX EF imaging system (Syngene). The results are shown in FIG. 3.

Figure 3:
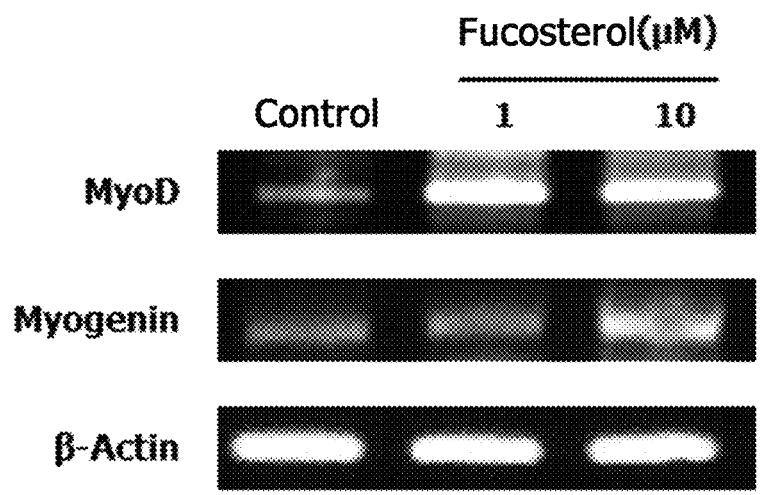
FIG. 3 shows results of measuring the mRNA expression of myoD and myogenin in L6 muscle cells when the L6 muscle cells are treated with fucosterol.

As a result, it can be seen that the mRNA expression of MyoD and myogenin in the L6 muscle cells increased when the L6 muscle cells were treated with fucosterol, as shown in FIG. 3. This indicates that the fucosterol of the present invention has an excellent ability of promoting muscle differentiation in muscle cells.

Example 7

Muscle Differentiation Activity of *Sargassum fulvellum* Extract

As muscle cells, L6 myoblasts (ATCC) were cultured in the same manner as in Example 6. Thereafter, each of the ethanol extract, ethyl acetate extract, hexane extract and hot water extract of *Sargassum fulvellum* prepared in Examples 1-2 to 1-5 was dissolved at a concentration of 10 μg/mL in DMEM (Hyclone) supplemented with 2% HS (Hyclone), and the cells were treated with each of the extracts to induce myotube differentiation. In this case, a group in which the cells were treated with 0.01% DMSO instead of the sample was used as the control. This procedure was carried out at an interval of 2 days for 6 days to differentiate the cells, and RT-PCR was performed in the same manner as in Example 6.

Figure 4:
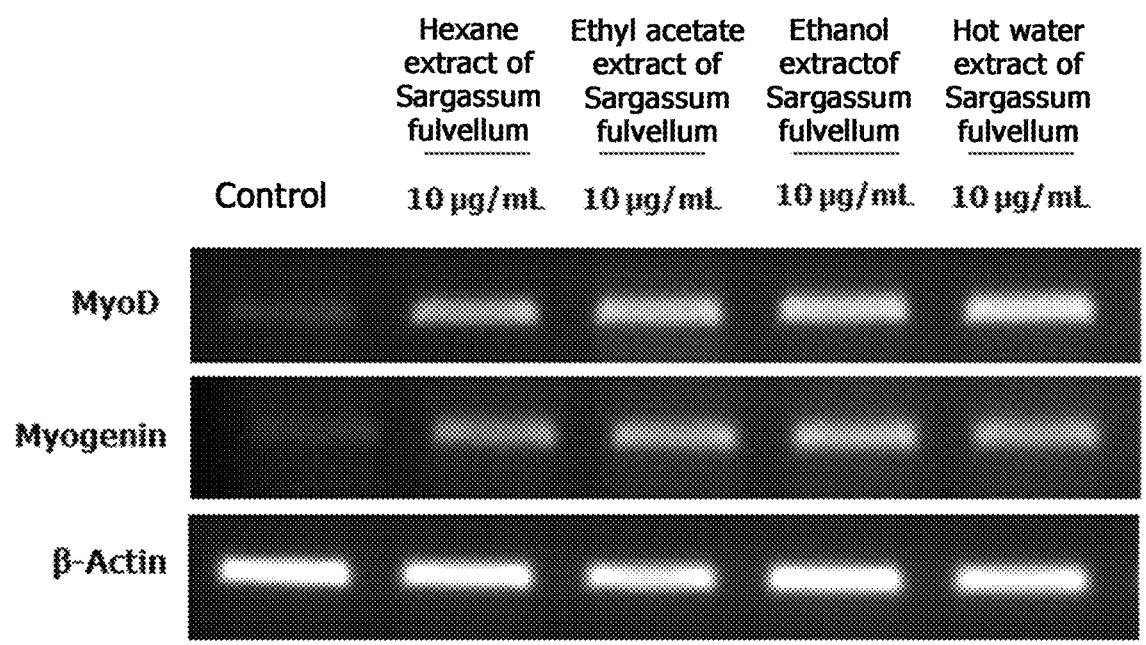
FIG. 4 shows results of measuring the mRNA expression of MyoD and myogenin in L6 muscle cells when the L6 muscle cells are treated with a hexane extract, an ethyl acetate extract, an ethanol extract, and a hot water extract of *Sargassum fulvellum*.

As a result, it can be seen that the mRNA expression of MyoD and myogenin in the L6 muscle cells increased when the L6 muscle cells were treated with the *Sargassum fulvellum* extract, as shown in FIG. 4. This indicates that the *Sargassum fulvellum* extract of the present invention has an excellent ability of promoting muscle differentiation in muscle cells.

Example 8

Muscle Differentiation Activity of *Sargassum fusiforme* Extract

As muscle cells, L6 myoblasts (ATCC) were cultured in the same manner as in Example 6. Thereafter, each of the ethanol extract, ethyl acetate extract, hexane extract and hot water extract of *Sargassum fusiforme* prepared in Examples 2-2 to 2-5 was dissolved at a concentration of 10 μg/mL in DMEM (Hyclone) supplemented with 2% HS (Hyclone), and the cells were treated with each of the extracts to induce myotube differentiation. In this case, a group in which the cells were treated with 0.01% DMSO instead of the sample was used as the control. This procedure was carried out at an interval of 2 days for 6 days to differentiate the cells, and RT-PCR was performed in the same manner as in Example 6.

Figure 5:
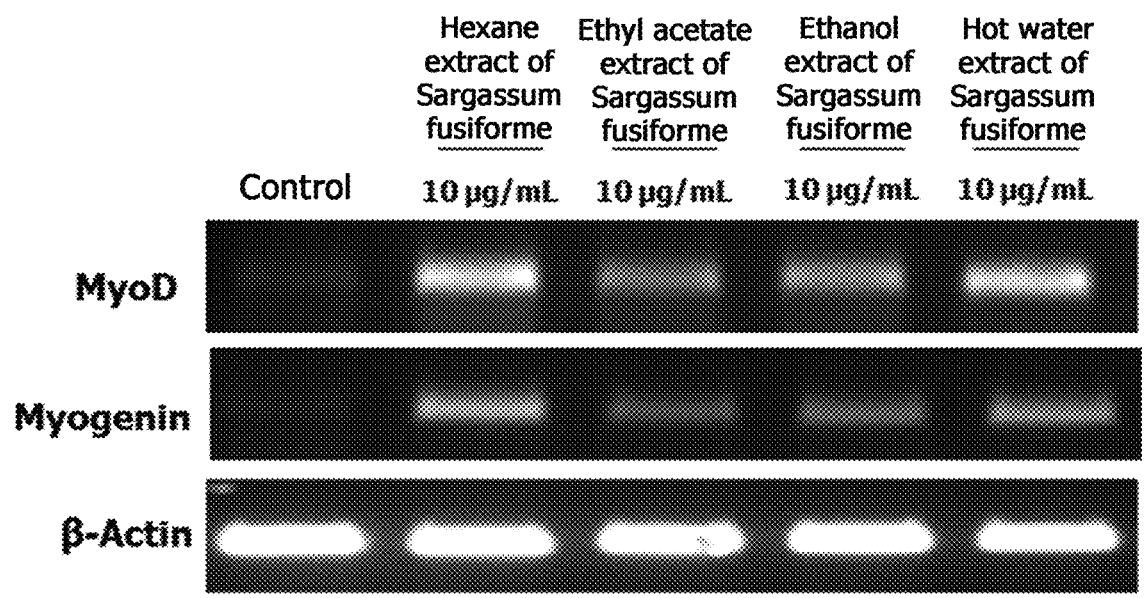
FIG. 5 shows results of measuring the mRNA expression of MyoD and myogenin in L6 muscle cells when the L6 muscle cells are treated with a hexane extract, an ethyl acetate extract, an ethanol extract, and a hot water extract of *Sargassum fusiforme*.

As a result, it can be seen that the mRNA expression of MyoD and myogenin in the L6 muscle cells increased when the L6 muscle cells were treated with the *Sargassum fusiforme* extract, as shown in FIG. 5. This indicates that the *Sargassum fusiforme* extract of the present invention has an excellent ability of promoting muscle differentiation in muscle cells.

Example 9

Muscle Protein Degradation-Inhibitory Activity of Fucosterol

As muscle cells, L6 myoblasts (ATCC) were added to a 6-well plate at a density of $2 \times 10^5$ cells/mL together with DMEM (Hyclone) supplemented with 10% FBS (Hyclone). When the cell density reached approximately 80 to 85%, the medium contained in the wells was removed, and the cells were treated with DMEM (Hyclone) supplemented with 2% HS (Hyclone) to induce myotube differentiation. Cell differentiation was performed for a total of 6 days while replacing the medium with a fresh medium every 2 days. After the differentiation, the fucosterol isolated and purified in Example 3 was dissolved at concentrations of 1 and 10 μM in DMEM (Hyclone) supplemented with 50 ng/mL of tumor necrosis factor alpha (TNF-α; PeproTech, Rocky Hills, N.J., USA), and the cells were then treated with the fucosterol. After 6 hours, total RNA was isolated using a TRIzol reagent (Invitrogen). The isolated total RNA was quantified using NanoDrop 1000 (Thermo Fisher Scientific Inc., MA, USA). 16 μL of the quantified RNA was synthesized into cDNA using Reverse Transcriptase Premix (ELPIS-Biotech) and a PCR machine (Gene Amp PCR System 2700; Applied Biosystems) under conditions of 42° C. and 55 minutes and 70° C. and 15 minutes. PCR was performed by repeating 30 cycles at 95° C. for 30 seconds, at 60° C. for 1 minute, and at 72° C. for 1 minute using 4 μL of cDNA (from 16 μL of the synthesized cDNA), the following specific primers (Bioneer), and a PCR premix (ELPIS-Biotech).

Atrogin-1:

Forward primer: 5'-CCCTGAGTGGCATCGCCCAA-3' (SEQ ID NO: 7)

Reverse primer: 5'-AGGTCCCGCCCATCGCTCA-3' (SEQ ID NO: 8)

MuRF-1:

Forward primer: 5'-GAAATGCTATGCAGAACCTG-3' (SEQ ID NO: 9)

Reverse primer: 5'-ATTCCTGCTTGTAGATGTCG-3' (SEQ ID NO: 10)

β-Actin:

Forward primer: 5'-AGCCATGTACGTAGCCATCC-3' (SEQ ID NO: 5)

Reverse primer: 5'-CTCTCAGCTGTGGTGCTGAA-3' (SEQ ID NO: 6)

The PCR-amplified cDNA was isolated by electrophoresis in a 1.5% agarose gel, and a cDNA band was confirmed using a G;BOX EF imaging system (Syngene). The results are shown in FIG. 6.

As a result, it can be seen that the mRNA expression of atrogin-1 and MuRF-1 in the L6 muscle cells decreased when the L6 muscle cells were treated with the fucosterol, as shown in FIG. 6. This indicates that the fucosterol of the present invention has an excellent ability of inhibiting the degradation of muscle proteins in muscle cells.

Example 10

Muscle Protein Degradation-Inhibitory Activity of *Sargassum fulvellum* Extract

Muscle cells were treated with DMEM (Hyclone) supplemented with 2% HS (Hyclone) in the same manner as in Example 9 to induce myotube differentiation. Thereafter, each of the ethanol extract, ethyl acetate extract, hexane extract and hot water extract of *Sargassum fulvellum* prepared in Examples 1-2 to 1-5 was dissolved at a concentration of 10 μg/mL in DMEM (Hyclone) supplemented with 50 ng/mL of TNF-α (PeproTech), and RT-PCR was then performed in the same manner as in Example 9.

As a result, it can be seen that the mRNA expression of atrogin-1 and MuRF-1 in the L6 muscle cells decreased when the L6 muscle cells were treated with the *Sargassum fulvellum* extract, as shown in FIG. 7. This indicates that the *Sargassum fulvellum* extract of the present invention has an excellent ability of inhibiting the degradation of muscle proteins in muscle cells.

Example 11

Muscle Protein Degradation-Inhibitory Activity of *Sargassum fusiforme* Extract

Muscle cells were treated with DMEM (Hyclone) supplemented with 2% HS (Hyclone) in the same manner as in Example 9 to induce myotube differentiation. Thereafter, each of the ethanol extract, ethyl acetate extract, hexane extract and hot water extract of *Sargassum fusiforme* prepared in Examples 2-2 to 2-5 was dissolved at a concentration of 10 μg/mL in DMEM (Hyclone) supplemented with 50 ng/mL of TNF-α (PeproTech), and RT-PCR was then performed in the same manner as in Example 9.

As a result, it can be seen that the mRNA expression of atrogin-1 and MuRF-1 in the L6 muscle cells decreased when the L6 muscle cells were treated with the ethanol extract, ethyl acetate extract, hexane extract and hot water extract of *Sargassum fusiforme*, as shown in FIG. 8. This indicates that the *Sargassum fusiforme* extract of the present invention has an excellent ability of inhibiting the degradation of muscle proteins in muscle cells.

Example 12

Muscle Development Activity of High-Pressure Extracts of *Sargassum fulvellum* and *Sargassum fusiforme*

Muscle cells were treated with the ultra-high pressure extract of *Sargassum fulvellum* prepared in Example 1-6, the supercritical fluid extract of *Sargassum fulvellum* prepared in Example 1-7, the subcritical fluid extract of *Sargassum fulvellum* prepared in Example 1-8, the ultra-high pressure extract of *Sargassum fusiforme* prepared in Example 2-6, the supercritical fluid extract of *Sargassum fusiforme* prepared in Example 2-7, and the subcritical fluid extract of *Sargassum fusiforme* prepared in Example 2-8 at a concentration of 20 ppm in the same manner as in Example 4. A p-mTOR protein band was chromogenically developed using an ECL Western blotting detection reagent (Amersham, Tokyo, Japan), and a density of the chromogenically developed protein band was measured using a G;BOX EF imaging system (Syngene, Cambridge, UK). In this case, the relative density of a protein band in an experimental group in which the cells are treated with the sample is indicated on a percentage (%) basis when it is assumed that the density of the control protein band is set to 100%. The results are listed in the following Table 1.

TABLE 1

Effect of high-pressure extracts of *Sargassum fulvellum* and *Sargassum fusiforme* on increase in protein expression level of p-mTOR

| Experimental group | Relative density (%) |
|---|---|
| Control | 100 |
| Example 1-6 | 131 |
| Example 1-7 | 129 |
| Example 1-8 | 143 |
| Example 2-6 | 128 |
| Example 2-7 | 140 |
| Example 2-8 | 133 |

As listed in Table 1, it can be seen that the ultra-high pressure extract, supercritical fluid extract, and subcritical fluid extract of *Sargassum fulvellum* and *Sargassum fusiforme* increased a protein expression level of p-mTOR which is a main gene involved in muscular function improvement.

Example 13

Confirmation of Effect of Increasing Muscle Mass in Animal Model

Five-week-old Wistar rats (Daehan Biolink, Korea) were adapted for one week, and fed 100 ng/g of TNF-α for 2 weeks to induce muscle atrophy. Thereafter, the rats were randomly divided into a total of 6 groups based on the weights thereof, each group consisting of 8 rats, which were then used in this experiment. As experimental groups, 500 mg/kg by weight of the dried powder of *Sargassum fulvellum*, 500 mg/kg by weight of the ethanol extract of *Sargassum fulvellum* prepared in Example 1-2, 500 mg/kg by weight of the dried powder of *Sargassum fusiforme*, 500 mg/kg by weight of the ethanol extract of *Sargassum fusiforme* prepared in Example 2-2, and 300 mg/kg by weight of the fucosterol prepared in Example 3 were dissolved in 0.25% carboxymethyl cellulose, and administered to the rats once a day for 8 weeks at a given time. In this case, a group in which TNF-α was added to the same amount of 0.25% carboxymethyl cellulose which the experimental group ingested was used as the control.

After the sample was administered for 8 weeks, muscles were incised from right lower calves of the rats, and weighed using a microbalance (Mettler PE160, USA). As a result, it was revealed that the weights of the muscles significantly ($p<0.01$) increased by 14.94%, 24.82%, 16.14%, 22.65%, and 25.78% in the groups in which the dried powder of *Sargassum fulvellum*, the ethanol extract of *Sargassum fulvellum*, the dried powder of *Sargassum fusiforme*, the ethanol extract of *Sargassum fusiforme*, and the fucosterol were administered to the rats, respectively, compared to the control, as listed in Table 2.

Such results indicate that the *Sargassum fulvellum*, the *Sargassum fulvellum* dried powder, the *Sargassum fulvellum* extract, the *Sargassum fusiforme*, the *Sargassum fusiforme* dried powder, the *Sargassum fusiforme* extract, or the fucosterol isolated from the extracts according to the present invention effectively function to increase muscle mass.

TABLE 2

Weights of calf muscles according to materials treated

| Experimental group | Mean weight of calf muscles (mg) |
| --- | --- |
| Control | 414.9 ± 20.3 |
| Dried powder of *Sargassum fulvellum* | 477.0 ± 19.8 |
| Ethanol extract of *Sargassum fulvellum* | 518.2 ± 23.6 |
| Dried powder of *Sargassum fusiforme* | 481.6 ± 31.1 |
| Ethanol extract of *Sargassum fusiforme* | 508.5 ± 22.8 |
| Fucosterol | 522.1 ± 30.6 |

Hereinafter, the preparative examples of foods and medicines, each of which include the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract according to the present invention as the active ingredient, will be described. However, it should be understood that the following examples are just preferred examples for the purpose of illustration only and are not intended to limit or define the scope of the invention. By using the fucosterol, the *Sargassum fulvellum* extract or the *Sargassum fusiforme* extract prepared in Examples 1 and 2, all of which had an excellent effect of preventing or alleviating muscle diseases or improving muscular function, the compositions such as medicines, foods, cosmetics and feed additives disclosed in Preparative Examples 1 to 4 were prepared using the components and composition ratios to be described below.

Preparative Example 1: Medicines

<1-1> Powder 50 mg of the fucosterol, the *Sargassum fulvellum* dried powder, the *Sargassum fulvellum* extract, the *Sargassum fusiforme* dried powder or the *Sargassum fusiforme* extract according to the present invention, and 2 g of crystalline cellulose were mixed, and the resulting mixture was then filled in an airtight pack to prepare a powder according to a conventional method of preparing a powder.

<1-2> Tablet 50 mg of the fucosterol, the *Sargassum fulvellum* dried powder, the *Sargassum fulvellum* extract, the *Sargassum fusiforme* dried powder or the *Sargassum fusiforme* extract according to the present invention, 400 mg of crystalline cellulose, and 5 mg of magnesium stearate were mixed, and the resulting mixture was then tablet-pressed to prepare a tablet according to a conventional method of preparing a tablet.

<1-3> Capsule 30 mg of the fucosterol, the *Sargassum fulvellum* dried powder, the *Sargassum fulvellum* extract, the *Sargassum fusiforme* dried powder or the *Sargassum fusiforme* extract according to the present invention, 100 mg of whey protein, 400 mg of crystalline cellulose, and 6 mg of magnesium stearate were mixed, and the resulting mixture was then filled in a gelatin capsule to prepare a capsule according to a conventional method of preparing a capsule.

<1-4> Injectable Solution

An injectable solution was prepared according to a conventional method of preparing an injectable solution by dissolving an active ingredient in distilled water for injections, adjusting a pH value of the solution to approximately pH 7.5, mixing 100 mg of the fucosterol of Example 3, distilled water for injections, and a pH control agent, and filling the resulting mixture in ampoules having a volume of 2 mL, and sterilizing the mixture.

Preparative Example 2: Foods

<2-1> Preparation of Health Food 1,000 mg of the fucosterol, the *Sargassum fulvellum* dried powder, the *Sargassum fulvellum* extract, the *Sargassum fusiforme* dried powder or the *Sargassum fusiforme* extract according to the present invention, 70 μg of vitamin A acetate, 1.0 mg of vitamin E, 0.13 mg of vitamin B1, 0.15 mg of vitamin B2, 0.5 mg of vitamin B6, 0.2 μg of vitamin B12, 10 mg of vitamin C, 10 μg of biotin, 1.7 mg of nicotinic acid amide, 50 μg of folic acid, 0.5 mg of calcium pantothenate, 1.75 mg of ferrous sulfate, 0.82 mg of zinc oxide, 25.3 mg of magnesium carbonate, 15 mg of potassium phosphate monobasic, 55 mg of potassium phosphate dibasic, 90 mg of potassium citrate, 100 mg of potassium carbonate, and 24.8 mg of magnesium chloride were mixed to prepare a health food. In this case, the blending ratios of the aforementioned components may be optionally modified. For example, the aforementioned components were mixed to prepare granules according to a conventional method of preparing a health food, and may be used to prepare a health food composition according to the conventional method.

<2-2> Preparation of Health Drink 1,000 mg of the fucosterol, the *Sargassum fulvellum* dried powder, the *Sargassum fulvellum* extract, the *Sargassum fusiforme* dried powder or the *Sargassum fusiforme* extract according to the present invention, 1,000 mg of citric acid, 100 g of oligosaccharides, 2 g of a plum concentrate, and 1 g of taurine were added to purified water, and mixed to prepare a total of 900 mL of the mixture according to a conventional method of preparing a health drink. Thereafter, the mixture was heated while stirring at 85° C. for approximately 1 hour, and the resulting solution was filtered, put into a sterile 2 L container, sealed, sterilized, and kept refrigerated. The solution may be used to prepare a health drink composition.

<2-3> Chewing Gum 0.1% by weight of the fucosterol, the *Sargassum fulvellum* dried powder, the *Sargassum fulvellum* extract, the *Sargassum fusiforme* dried powder or the *Sargassum fusiforme* extract according to the present invention was blended with 20% by weight of a gum base, 76.9% by weight of sugar, 1% by weight of a flavoring agent, and 2% by weight of water to prepare chewing gum according to a conventional method.

<2-4> Candy 0.1% by weight of the fucosterol, the *Sargassum fulvellum* dried powder, the *Sargassum fulvellum* extract, the *Sargassum fusiforme* dried powder or the *Sargassum fusiforme* extract according to the present invention was blended with 60% by weight of sugar, 39.8% by weight of starch syrup, and 0.1% by weight of a flavoring agent to prepare candy according to a conventional method.

<2-5> Biscuit 0.8301% by weight of the fucosterol, the *Sargassum fulvellum* dried powder, the *Sargassum fulvellum* extract, the *Sargassum fusiforme* dried powder or the *Sargassum fusiforme* extract according to the present invention was blended with 25.59% by weight of grade 1 cake flour, 22.22% by weight of grade 1 plain flour, 4.80% by weight of refined sugar, 0.73% by weight of saline, 0.78% by weight of glucose, 11.78% by weight of palm shortening, 1.54% by weight of ammonium, 0.17% by weight of sodium bicarbonate, 0.16% by weight of sodium bisulfite, 1.45% by weight of rice flour, 0.0001% by weight of vitamin B, 0.04% by weight of milk flavoring, 20.6998% by weight of water, 1.16% by weight of whole milk powder, 0.29% by weight of alternative milk powder, 0.03% by weight of calcium phosphate monobasic, 0.29% by weight of spray salt, and 7.27% by weight of milk spray to prepare biscuits according to a conventional method.

Preparative Example 3: Cosmetics

<3-1> Nourishing Toner (Milk Lotion)

The fucosterol, the *Sargassum fulvellum* dried powder, the *Sargassum fulvellum* extract, the *Sargassum fusiforme* dried powder or the *Sargassum fusiforme* extract according to the present invention was mixed with the components of a nourishing toner formulation at the ratios listed in the following Table 3 to prepare a nourishing toner according to a conventional method.

TABLE 3

| Blending component | Preparative Example 3-1 (% by weight) |
|---|---|
| Fucosterol, *Sargassum fulvellum* dried powder, *Sargassum fulvellum* extract, *Sargassum fusiforme* dried powder or *Sargassum fusiforme* extract | 2.0 |
| Squalane | 5.0 |
| Beeswax | 4.0 |
| Polysorbate 60 | 1.5 |
| Sorbitan sesquioleate | 1.5 |
| Liquid paraffin | 0.5 |
| Caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, pigment, and flavoring agent | Suitable amount |
| Purified water | to 100 |

<3-2> Emulsifying Toner (Skin Lotion)

The fucosterol, the *Sargassum fulvellum* dried powder, the *Sargassum fulvellum* extract, the *Sargassum fusiforme* dried powder or the *Sargassum fusiforme* extract according to the present invention was mixed with the components of an emulsifying toner formulation at the ratios listed in the following Table 4 to prepare an emulsifying toner according to a conventional method.

TABLE 4

| Blending component | Preparative Example 3-2 (% by weight) |
|---|---|
| Fucosterol, *Sargassum fulvellum* dried powder, *Sargassum fulvellum* extract, *Sargassum fusiforme* dried powder or *Sargassum fusiforme* extract | 2.0 |
| Glycerin | 3.0 |
| Butylene glycol | 2.0 |
| Propylene glycol | 2.0 |
| Carboxyvinyl polymer | 0.1 |
| PEG 12 nonylphenyl ether | 0.2 |
| Polysorbate 80 | 0.4 |
| Ethanol | 10.0 |
| Triethanolamine | 0.1 |
| Preservative, pigment, and flavoring agent | Suitable amount |
| Purified water | to 100 |

<3-3> Nourishing Cream

The fucosterol, the *Sargassum fulvellum* dried powder, the *Sargassum fulvellum* extract, the *Sargassum fusiforme* dried powder or the *Sargassum fusiforme* extract according to the present invention was mixed with the components of a nourishing cream formulation at the ratios listed in the following Table 5 to prepare a nourishing cream according to a conventional method.

TABLE 5

| Blending component | Preparative Example 3-3 (% by weight) |
|---|---|
| Fucosterol, *Sargassum fulvellum* dried powder, *Sargassum fulvellum* extract, *Sargassum fusiforme* dried powder or *Sargassum fusiforme* extract | 2.0 |
| Polysorbate 60 | 1.5 |
| Sorbitan sesquioleate | 0.5 |
| PEG60 hydrogenated castor oil | 2.0 |
| Liquid paraffin | 10 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Preservative | Suitable amount |
| Pigment | Suitable amount |
| Flavoring agent | Suitable amount |
| Purified water | to 100 |

<3-4> Massage Cream

The fucosterol, the *Sargassum fulvellum* dried powder, the *Sargassum fulvellum* extract, the *Sargassum fusiforme* dried powder or the *Sargassum fusiforme* extract according to the present invention was mixed with the components of a massage cream formulation at the ratios listed in the following Table 6 to prepare a massage cream according to a conventional method.

TABLE 6

| Blending component | Preparative Example 3-4 (% by weight) |
|---|---|
| Fucosterol, *Sargassum fulvellum* dried powder, *Sargassum fulvellum* extract, *Sargassum fusiforme* dried powder or *Sargassum fusiforme* extract | 1.0 |
| Beeswax | 10.0 |
| Polysorbate 60 | 1.5 |
| PEG 60 hydrogenated castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Preservative, pigment, and flavoring agent | Suitable amount |
| Purified water | to 100 |

<3-5> Pack

The fucosterol, the *Sargassum fulvellum* dried powder, the *Sargassum fulvellum* extract, the *Sargassum fusiforme* dried powder or the *Sargassum fusiforme* extract according to the present invention was mixed with the components of a pack formulation at the ratios listed in the following Table 7 to prepare a pack according to a conventional method.

TABLE 7

| Blending component | Preparative Example 3-5 (% by weight) |
|---|---|
| Fucosterol, *Sargassum fulvellum* dried powder, *Sargassum fulvellum* extract, *Sargassum fusiforme* dried powder or *Sargassum fusiforme* extract | 1.0 |
| Polyvinyl alcohol | 13.0 |
| Sodium carboxymethyl cellulose | 0.2 |
| Glycerin | 5.0 |
| Allantoin | 0.1 |
| Ethanol | 6.0 |
| PEG 12 nonylphenyl ether | 0.3 |
| Polysorbate 60 | 0.3 |
| Preservative, pigment, and flavoring agent | Suitable amount |
| Purified water | to 100 |

<3-6> Gel

The fucosterol, the *Sargassum fulvellum* dried powder, the *Sargassum fulvellum* extract, the *Sargassum fusiforme* dried powder or the *Sargassum fusiforme* extract according to the present invention was mixed with the components of a gel formulation at the ratios listed in the following Table 8 to prepare a gel according to a conventional method.

TABLE 8

| Blending component | Preparative Example 3-6 (% by weight) |
|---|---|
| Fucosterol, *Sargassum fulvellum* dried powder, *Sargassum fulvellum* extract, *Sargassum fusiforme* dried powder or *Sargassum fusiforme* extract | 0.5 |
| Ethylenediamine sodium acetate | 0.05 |
| Glycerin | 5.0 |
| Carboxyvinyl polymer | 0.3 |
| Ethanol | 5.0 |
| PEG 60 hydrogenated castor oil | 0.5 |
| Triethanolamine | 0.3 |
| Preservative, pigment, and flavoring agent | Suitable amount |
| Purified water | to 100 |

Preparative Example: Feed

<4-1> Preparation of Feed Additive

The fucosterol, the *Sargassum fulvellum* dried powder, the *Sargassum fulvellum* extract, the *Sargassum fusiforme* dried powder or the *Sargassum fusiforme* extract according to the present invention was mixed with the blending components listed in the following Table 9 to prepare a feed additive according to a conventional method.

TABLE 9

| Blending component | Preparative Example 4-1 (weight (g)) |
|---|---|
| Fucosterol, *Sargassum fulvellum* dried powder, *Sargassum fulvellum* extract, *Sargassum fusiforme* dried powder or *Sargassum fusiforme* extract | 100 g |
| Excipient | Suitable amount |

<4-2> Preparation of Feed

The fucosterol, the *Sargassum fulvellum* dried powder, the *Sargassum fulvellum* extract, the *Sargassum fusiforme* dried powder or the *Sargassum fusiforme* extract according to the present invention was mixed with the blending components listed in the following Table 10 to prepare feed according to a conventional method.

TABLE 10

| Blending component | Preparative Example 4-2 (weight (g)) |
|---|---|
| Fucosterol, *Sargassum fulvellum* dried powder, *Sargassum fulvellum* extract, *Sargassum fusiforme* dried powder or *Sargassum fusiforme* extract | 50 g |
| Mushroom medium | 200 g |
| Wheat bran | 30 g |
| Beet pulp | 50 g |
| Spent grain | 220 g |
| Corn flakes | 200 g |
| Full-fat soybean | 40 g |
| Starch pulp | 100 g |
| Corn silage | 200 g |
| Corn cob | 180 g |
| Bean-curd dregs | 400 g |
| Ryegrass | 323 g |
| Zeolite | 14 g |
| Tapioca | 40 g |

As described above, the present invention provides a composition for preventing or treating muscle diseases or improving muscular function, which includes fucosterol, *Sargassum fulvellum*, a *Sargassum fulvellum* dried powder, a *Sargassum fulvellum* extract, *Sargassum fusiforme*, a *Sargassum fusiforme* dried powder or a *Sargassum fusiforme* extract. More specifically, the fucosterol, the *Sargassum fulvellum*, the *Sargassum fulvellum* dried powder, the *Sargassum fulvellum* extract, the *Sargassum fusiforme*, the *Sargassum fusiforme* dried powder or the *Sargassum fusiforme* extract according to the present invention has an excellent effect of preventing, alleviating or treating muscle diseases or improving muscular function by increasing the protein expression of p-mTOR which is a main gene involved in muscle protein synthesis, inhibiting the mRNA expression of MuRF-1 and atrogin-1 involved in muscle protein degradation, and increasing the mRNA expression of MyoD and myogenin involved in muscle differentiation. Also, the composition of the present invention can be safely used without side effects because the composition is a natural product, and can be highly industrially applicable because a composition having an excellent effect of preventing, alleviating or treating muscle diseases or improving muscular function can be provided.

The invention claimed is:

1. A method of preventing or treating sarcopenia a muscle disease, or improving muscular function, the method comprising administering to a subject in need thereof, a composition comprising a fucosterol compound represented by the following Formula 1 or a *Sargassum fulvellum* or *Sargassum fusiforme* extract comprising the fucosterol compound represented by the following Formula 1

[Formula 1]

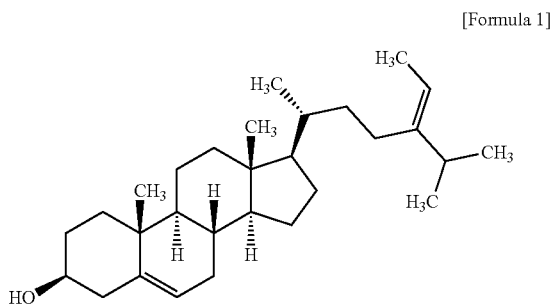

wherein the subject has decreased p-mTOR, decreased MyoD, decreased myogenin, increased MuRF-1, and increased atrogin-1 compared to a subject without sarcopenia, wherein the administration of the composition (i) increases muscle development, (ii) inhibits degradation of muscle proteins, and (iii) increases muscle mass of the subject.

2. The method of claim 1, wherein the composition comprises the fucosterol compound represented by Formula 1, and wherein the compound is isolated from *Sargassum fulvellum* or *Sargassum fusiforme* extract.

3. The method of claim 1, wherein the composition comprises the extract from *Sargassum fulvellum* or *Sargassum fusiforme*.

4. The method of claim 3, wherein the extract is obtained by extracting *Sargassum fulvellum* or *Sargassum fusiforme* with one or more solvents selected from the group consisting of water, an organic solvent having 1 to 6 carbon atoms, a subcritical fluid, and a supercritical fluid.

5. The method of claim 4, wherein the extract is obtained with the organic solvent having 1 to 6 carbon atoms, wherein the organic solvent comprises one or more solvents selected from the group consisting of an alcohol having 1 to 6 carbon atoms, acetone, ether, benzene, chloroform, ethyl acetate, methylene chloride, hexane, cyclohexane, and petroleum ether.

6. The method of claim 3, wherein the extract is obtained by extracting *Sargassum fulvellum* or *Sargassum fusiforme* under a condition of an ultra-high pressure of 100 MPa to 1,000 MPa.

7. The method of claim 1, wherein the composition is a pharmaceutical composition that is topically, orally, or parenterally administered to the subject.

8. The method of claim 1, wherein the composition is a health functional food that is orally administered to the subject.

9. The method of claim 1, wherein the composition is a cosmetic composition that is topically administered to the subject.

10. The method of claim 1, wherein the composition is a feed additive that is orally administered to the subject.

11. The method of claim 1, wherein the composition increases protein expression of p-mTOR in the subject.

12. The method of claim 1, wherein the composition inhibits mRNA expression of MuRF-1 and atrogin-1 in the subject.

13. The method of claim 1, wherein the composition increases mRNA expression of MyoD and myogenin in the subject.

* * * * *

SEQUENCE LISTING

<160> NUMBER OF SEQ ID NOS: 10

<210> SEQ ID NO 1
<211> LENGTH: 20
<212> TYPE: DNA

```
<213> ORGANISM: Artificial Sequence
<220> FEATURE:
<223> OTHER INFORMATION: MyoD forward primer

<400> SEQUENCE: 1
tttcgactca ccagacctgc                                               20

<210> SEQ ID NO 2
<211> LENGTH: 20
<212> TYPE: DNA
<213> ORGANISM: Artificial Sequence
<220> FEATURE:
<223> OTHER INFORMATION: MyoD reverse primer

<400> SEQUENCE: 2
cagagcctgc agaccttcaa                                               20

<210> SEQ ID NO 3
<211> LENGTH: 20
<212> TYPE: DNA
<213> ORGANISM: Artificial Sequence
<220> FEATURE:
<223> OTHER INFORMATION: Myogenin forward primer

<400> SEQUENCE: 3
tttcgcacct gatggacctg                                               20

<210> SEQ ID NO 4
<211> LENGTH: 20
<212> TYPE: DNA
<213> ORGANISM: Artificial Sequence
<220> FEATURE:
<223> OTHER INFORMATION: Myogenin reverse primer

<400> SEQUENCE: 4
ctttcttgag cctgcgcttc                                               20

<210> SEQ ID NO 5
<211> LENGTH: 20
<212> TYPE: DNA
<213> ORGANISM: Artificial Sequence
<220> FEATURE:
<223> OTHER INFORMATION: Beta-actin forward primer

<400> SEQUENCE: 5
agccatgtac gtagccatcc                                               20

<210> SEQ ID NO 6
<211> LENGTH: 20
<212> TYPE: DNA
<213> ORGANISM: Artificial Sequence
<220> FEATURE:
<223> OTHER INFORMATION: Beta-actin reverse primer

<400> SEQUENCE: 6
ctctcagctg tggtgctgaa                                               20

<210> SEQ ID NO 7
<211> LENGTH: 20
<212> TYPE: DNA
<213> ORGANISM: Artificial Sequence
<220> FEATURE:
<223> OTHER INFORMATION: Atrogin-1 forward primer

<400> SEQUENCE: 7
ccctgagtgg catcgcccaa                                               20
```

```
<210> SEQ ID NO 8
<211> LENGTH: 19
<212> TYPE: DNA
<213> ORGANISM: Artificial Sequence
<220> FEATURE:
<223> OTHER INFORMATION: Atrogin-1 reverse primer

<400> SEQUENCE: 8
aggtcccgcc catcgctca                                           19

<210> SEQ ID NO 9
<211> LENGTH: 20
<212> TYPE: DNA
<213> ORGANISM: Artificial Sequence
<220> FEATURE:
<223> OTHER INFORMATION: MuRF-1 forward primer

<400> SEQUENCE: 9
gaaatgctat gcagaacctg                                          20

<210> SEQ ID NO 10
<211> LENGTH: 20
<212> TYPE: DNA
<213> ORGANISM: Artificial Sequence
<220> FEATURE:
<223> OTHER INFORMATION: MuRF-1 reverse primer

<400> SEQUENCE: 10
attcctgctt gtagatgtcg                                          20
```